United States Patent
Yamakawa et al.

(10) Patent No.: US 8,795,158 B2
(45) Date of Patent: Aug. 5, 2014

(54) ENDOSCOPE INSERTION ASSISTING DEVICE

(75) Inventors: Shinichi Yamakawa, Kanagawa (JP); Tsuyoshi Ashida, Kanagawa (JP); Takayuki Nakamura, Kanagawa (JP); Yasunori Ohta, Kanagawa (JP); John J. Allen, Mendota Heights, MN (US); Charles Alan Brantingham, St. Paul, MN (US)

(73) Assignee: FUJIFILM Corporation, Tokyo (JP)

( * ) Notice: Subject to any disclaimer, the term of this patent is extended or adjusted under 35 U.S.C. 154(b) by 24 days.

(21) Appl. No.: 13/455,172

(22) Filed: Apr. 25, 2012

(65) Prior Publication Data

US 2012/0277530 A1 Nov. 1, 2012

Related U.S. Application Data

(60) Provisional application No. 61/479,250, filed on Apr. 26, 2011.

(51) Int. Cl.
*A61B 1/04* (2006.01)
*A61B 1/01* (2006.01)
*A61B 1/00* (2006.01)

(52) U.S. Cl.
CPC .............. *A61B 1/0016* (2013.01); *A61B 1/01* (2013.01); *A61B 1/0008* (2013.01); *A61B 1/00135* (2013.01)
USPC ............................ 600/114; 600/127; 600/129

(58) Field of Classification Search
CPC .. A61B 1/00135; A61B 1/00156; A61B 1/01; A61B 1/0016; A61B 1/0008
USPC ................. 600/106, 146, 159, 114, 127, 129; 356/241.1, 241.3–241.6
See application file for complete search history.

(56) References Cited

U.S. PATENT DOCUMENTS

| 5,409,305 A * | 4/1995 | Nagorcka | 305/116 |
| 2003/0216616 A1* | 11/2003 | Krupa et al. | 600/140 |
| 2006/0089533 A1* | 4/2006 | Ziegler et al. | 600/114 |
| 2010/0210900 A1* | 8/2010 | Allen et al. | 600/101 |

FOREIGN PATENT DOCUMENTS

JP 2009-513250 A 4/2009

* cited by examiner

*Primary Examiner* — Alireza Nia
*Assistant Examiner* — Timothy J Neal
(74) *Attorney, Agent, or Firm* — Birch, Stewart, Kolasch & Birch, LLP

(57) ABSTRACT

An insertion assisting device includes a rotary body in the form of toroid, and a support and drive part for supporting the rotary body in a rotatable manner and rotating it. The support and drive part has an approximately cylindrical supporting member for supporting the rotary body in a rotatable manner. The rotary body is provided with a convex portion for increasing the thickness to improve the strength thereof. A concave portion having a shape corresponding to the shape of the convex portion is formed on a portion of a front end surface of the supporting member, which is made in contact with the convex portion. The concave portion prevents the rotary body from stopping rotating, which may be caused by point contact between the convex portion and the supporting member.

14 Claims, 12 Drawing Sheets

ENDOSCOPE INSERTION ASSISTING DEVICE

CROSS REFERENCE TO RELATED APPLICATION

This nonprovisional application claims the benefit under 35 U.S.C. §119(e) of U.S. Provisional Application No. 61/479,250 filed on Apr. 26, 2011. The entire content of all of the above application is hereby incorporated by reference.

BACKGROUND OF THE INVENTION

1. Field of the Invention

The present invention relates to an endoscope insertion assisting device for assisting insertion of an endoscope into a body cavity.

2. Description of the Related Art

An endoscope consists of an insertion section to be inserted into a body cavity, and an operating section for operating the insertion section. In an endoscopy, in particular, in a colorectal examination, since the large intestine has a winding structure in the body cavity, and is flexible and is fixed at only a few positions in the body cavity, the insertion operation of the endoscope is very difficult. Therefore, a lot of experience is required to acquire skills for inserting the endoscope into the large intestine. When the insertion skills are not sufficient, a test subject may suffer from great pain.

It is said that the most difficult part in the large intestine for insertion of the endoscope is so-called sigmoid colon and transverse colon, because of the following reasons. Unlike the other parts, the sigmoid colon and transverse colon are not fixed inside the body cavity, and therefore they may arbitrarily change in shape within a range of their own lengths, or may change in shape inside the body cavity due to contact force upon insertion of the endoscope. In view of the above, a lot of skills for making the sigmoid colon and transverse colon straight have been proposed, so as to reduce the contact between the endoscope and bowels at the time of inserting the endoscope as much as possible.

Further, there has been proposed a device for enabling an endoscope to be self-propelled in an insertion direction inside the bowels, so as to make it easy to insert the endoscope, even if the insertion skills are not sufficient. For example, Japanese Patent Translation Publication No. 2009-513250 discloses an endoscope insertion assisting device, in which a rotary body in the form of toroid (hollow cylinder) is rotated so as to cause friction force between an outer surface of the rotary body and bowel walls, and due to the friction force, propulsive force in an insertion direction is obtained.

In the insertion assisting device according to the above patent document, a cylindrical supporting member provided in a space inside the rotary body supports the rotary body in a rotatable manner, and the rotary body is sandwiched between driving gears disposed so as to come in contact with the outer surface of the rotary body rotating inside the supporting member and driven rollers disposed so as to be opposed to the driving gears across the rotary body, such that the rotary body rotates.

When the rotary body of the insertion assisting device configured as described above is thick and does not have sufficient flexibility, resist becomes larger at a front turned edge, a rear turned edge, and a driving section, and thereby the rotary body cannot rotate smoothly. In contrast, when the rotary body is thin and does not have sufficient strength, the driving force from the driving gears may not be adequately transmitted to the rotary body, or the rotary body may be broken due to friction at the driving section.

In view of the above, the thickness of a portion of the rotary body of the insertion assisting device, which is made in contact with the driving section, is made larger than those of other portions of the rotary body, such that a balance between the strength necessary for the driving and flexibility necessary for the smooth rotation is kept. In this case, each of the portions made thicker has a belt-like shape formed along a rotational direction of the rotary body. Accordingly, there are thick portions and thin portions along the circumferential direction of the rotary body. For example, according to the above patent document, the driving is performed in three portions, and therefore the thick portions are arranged at intervals of approximately 120 degrees in the circumferential direction of the rotary body.

However, in the case where there are the thick portions and the thin portions along the circumferential direction of the rotary body as described above, when the front end of the supporting member comes in contact with the inner wall surface of the body cavity, the thick portions of the rotary body come in point contact with the front end of the supporting member. Since the pressure is focused on the spot at which the point contact occurs, the rotary body is more likely to stop rotating by being influenced by the contact pressure in comparison with a rotary body having a uniform thickness.

When the rotary body stops rotating by being influenced by the contact pressure during the driving of the driving gears, holes may be made in the rotary body by idle rotation of the driving gears. Additionally, when a certain portion of the rotary body stops rotating, other portions of the rotary body may be forcibly advanced and drawn-in between the driving gears and the driven rollers to get stuck therebetween. In this case, even after the contact pressure is decreased, the rotary body cannot not rotate.

SUMMARY OF THE INVENTION

An object of the present invention is to provide an endoscope insertion assisting device in which a rotary body does not stop upon contact of a front end of a supporting member with an inner wall surface of a body cavity.

In order to achieve the above object, an endoscope insertion assisting device of the present invention includes a supporting member, a rotary body, a concave portion, a driving member, a pressing member, and an attachment portion. The supporting member has an approximately cylindrical shape. The rotary body is formed into a toroid or a belt. The rotary body is wound over the supporting member and supported in a rotatable manner so as to rotate inside and outside the supporting member in a circulating manner. The rotary body includes a first area continuously formed to have a fixed thickness along the rotational direction, and a second area continuously formed to have a convex portion projected more than said first area along the rotational direction. The second area has an increased thickness so as to make strength thereof higher than that of the first area. A concave portion for guiding a protrusion of the rotary body is disposed on a front end surface of the supporting member. The driving member is disposed so as to come in contact with the second area of the rotary body, and transmits the driving force to the rotary body. The pressing member is disposed so as to face the driving member across the rotary body. The pressing member presses the rotary body against the driving member such that the driving force from the driving member is adequately transmitted to the rotary body. The attachment portion is used for detachably attaching the supporting member to an insertion section of an endoscope, in a state that the rotational direction of the rotary body is approximately coincident with an insertion direction of the insertion section.

The concave portion preferably has a size corresponding to the convex portion, such that the first area and the second area are on an approximately same plane of an outer surface of the rotary body when an inner surface of the rotary body comes in contact with the front end surface of the supporting member.

Preferably, the convex portion is provided with a streaky protrusion protruding along the rotational direction, and the concave portion is provided with a groove having a shape corresponding to the protrusion. The groove is preferably continuously formed in an inner surface of the supporting member. The cross-sectional shape of the convex portion is preferably a circular arc in which a height thereof is the largest at the center in a direction approximately orthogonal to the rotational direction and the height thereof is gradually decreased toward both side ends.

Preferably, the rotary body is formed into a toroid, and provided with a plurality of the first areas and a plurality of the second areas alternately arranged in a circumferential direction thereof, and a plurality of the driving members and a plurality of the pressing members are provided so as to correspond to each of the second areas.

Preferably, the first area consists of a first layer made of a resin material having bendability and flexibility, and the second area consists of a two-layer structure including the first layer and a second layer. The second layer has a low flexural modulus and a high tensile modulus so as to prevent the first layer from being stretched in the rotational direction.

The supporting member preferably consists of a main body made of a metal material or a resin material, and a pair of contact protecting portions made of a resin material and attached to a front end and a rear end of the main body. The concave portion is formed on the front end surface of the contact protecting portion attached to the front end of the main body.

Preferably, the driving member is a worm wheel, and the pressing member is a driven roller attached to the supporting member. Further, the driven roller is preferably provided with a groove having a small diameter for receiving the protrusion of the rotary body.

Preferably, the endoscope insertion assisting device further includes a gear barrel rotating by driving force from an external driving source, a worm formed at an outer periphery of the gear barrel so as to rotate the worm wheel, and a cylindrical holding member disposed between the gear barrel and the supporting member so as to hold the driving member in a state that the diving member is exposed through an outer surface of the holding member.

The attachment portion preferably has a shaft barrel for supporting the gear barrel in a rotatable manner.

According to the present invention, since the rotary body is provided with the first area and the second area thicker than the first area, it is possible to improve the strength and flexibility of the rotary body at the same time. Further, according to the present invention, since there is provided the concave portion into which the second area on the front end surface of the supporting member enters, even when the front end of the supporting member comes in contact with the inner wall surface of the body cavity, it is possible to prevent point contact between the front end of the supporting member and the second area. Thereby, it is possible to prevent the rotary body from stopping rotating.

BRIEF DESCRIPTION OF THE DRAWINGS

The above object and advantages can be easily understood by those skilled in the art by reading the detailed description of the preferred embodiments of the present invention with reference to the attached drawings.

DESCRIPTION OF THE PREFERRED EMBODIMENTS

Figure 1:
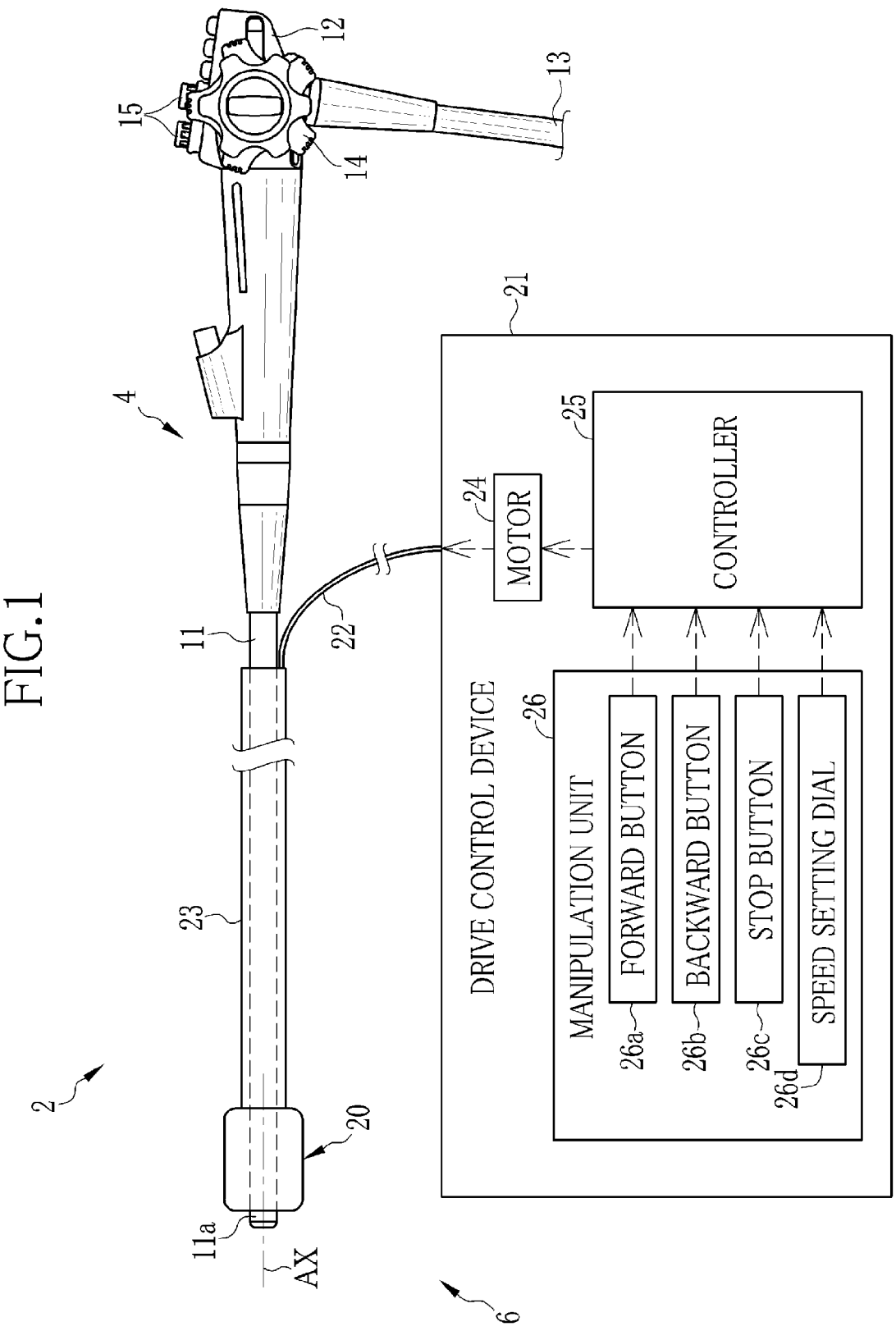
FIG. 1 is an explanatory view schematically showing a structure of an endoscope system.

As shown in FIG. 1, an endoscope system 2 consists of an electronic endoscope (hereinafter abbreviated as endoscope) 4 for observing the inside of a body cavity of a test subject, and an insertion assisting unit 6 for assisting insertion of the endoscope 4 into the body cavity. The endoscope 4 includes an insertion section 11, an operation section 12, and a universal cord 13. The insertion section 11 incorporates a solid-state imaging device such as CCD sensor and CMOS sensor, and is inserted into alimentary canals such as the large intestine. The operation section 12 is used for the grip of the endoscope 4 and the operation of the insertion section 11. The universal cord 13 connects the endoscope 4 to a processor device and a light source device (not shown in the drawing).

The insertion section 11 is a flexible rod-shaped body. As is well known, a distal portion 11a of the insertion section 11 includes an image capturing window for capturing a subject image, an illumination window for projecting illumination light, an air/water nozzle for ejecting air and water, and the like (not shown in the drawing). The operation section 12 includes an angle knob 14, operation buttons 15, and the like. The angle knob 14 is caused to rotate at the time of adjusting the curving direction and curving amount of the insertion section 11. The operation buttons 15 are used for various operations, such as air sending, water sending, and suction.

The universal cord 13 is connected to the operation section 12. The universal cord 13 incorporates, for example, a signal cable for outputting an image signal from the solid-state imaging device to the processor device, a light guide for guiding light projected from the light source device to the distal portion 11a, an air/water channel for sending air and water to the distal portion 11a, and the like.

The insertion assisting unit 6 consists of an insertion assisting device (self-propelling device) 20, a drive control device 21, a torque wire 22, and an overtube 23. The insertion assisting device 20 is detachably attached to the distal portion 11a of the insertion section 11, and advances or retracts the insertion section 11 in the alimentary canals, for example. The drive control device 21 drives the insertion assisting device 20 by supplying mechanical driving force thereto, and controls the insertion assisting device 20 so as to advance, retract, or stop it.

The torque wire 22 transmits driving force from the drive control device 21 to the insertion assisting device 20. The torque wire 22 is covered with a protective sheath (not shown in the drawing) over its entire length. The torque wire 22 rotates inside the protective sheath, and thereby transmits the driving force of the drive control device 21 to the insertion assisting device 20. Further, the torque wire 22 is detachably connected to the drive control device 21 through a well-known connector or the like.

The overtube 23 is fitted onto the insertion section 11. The overtube 23 covers the insertion section 11 and the torque wire 22, and as the torque wire 22 is made to extend along the insertion section 11, the insertion section 11 and the torque wire 22 are put together. If so, the insertion section 11 and the torque wire 22 do not come apart within a body cavity, and handling of those can be facilitated. Note that, the overtube 23 is not limited to one which covers from the distal end of the insertion section 11 to the proximal end thereof. For example, the overtube 23 may be short so as to cover only the distal end of the insertion section 11 and thereround. Additionally, if the torque wire 22 does not get in the way, the overtube 23 is not necessarily provided.

The drive control device 21 consists of a motor 24, a controller 25, and a manipulation unit 26. The motor 24 is a power source for generating the driving force for driving the insertion assisting device 20. The controller 25 controls the driving of the motor 24. The manipulation unit 26 is used to input operation instructions to the controller 25. A rotating shaft of the motor 24 is coupled to an end portion of the torque wire 22 through a gear or a connector, such that the driving force generated by the motor 24 is transmitted to the torque wire 22. Accordingly, the driving force of the motor 24 is transmitted to the insertion assisting device 20 through the torque wire 22.

The manipulation unit 26 is equipped with an forward button 26a for instructing the insertion assisting device 20 to advance, a backward button 26b for instructing the insertion assisting device 20 to retract, a stop button 26c for instructing the insertion assisting device 20 to stop, and a speed setting dial 26d for changing the movement speed of the insertion assisting device 20. Each of the buttons 26a to 26c and the speed setting dial 26d are electrically connected to the controller 25 so as to input the result of the operation instructions to the controller 25. In response to the input from the manipulation unit 26, the controller 25 controls the rotation and stop of the motor 24 as well as the rotational direction and the rotational speed thereof.

Figure 2:
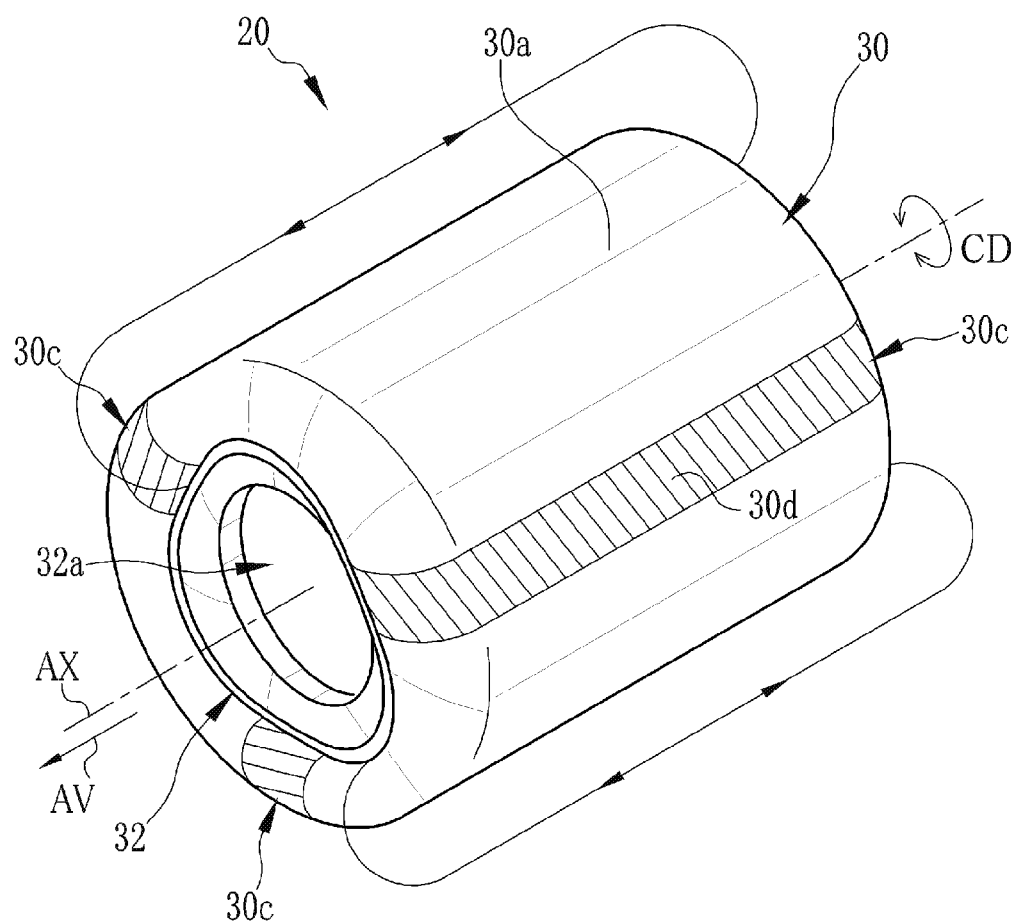
FIG. 2 is a perspective view of an insertion assisting device.

As shown in FIG. 2, the insertion assisting device 20 includes a rotary body 30 and a support and drive part 32. The rotary body 30 is made of a flexible material and shaped into a toroid (hollow cylinder). The rotary body 30 rotates such that an outer surface 30a thereof circulates around itself in a direction along a central axis of the rotary body 30, so as to generate propulsive force for advancing or retracting the insertion section 11 inside the alimentary canals. The support and drive part 32 supports the rotary body 30 in a rotatable manner, and transmits the driving force received from the drive control device 21 through the torque wire 22 to the rotary body 30, so as to rotate the rotary body 30.

The support and drive part 32 has an attachment portion 32a for detachably attaching the insertion assisting device 20 to the insertion section 11 of the endoscope 4. The attachment portion 32a is a through hole having a cross-section of approximately circular shape and formed in a direction along an insertion axis AX. The diameter of the attachment portion 32a is approximately the same as that of the insertion section 11. The insertion assisting device 20 is detachably attached to the insertion section 11 so as not to be removed from the insertion section 11 by fitting the insertion section 11 into the attachment portion 32a in a state that the rotational direction of the rotary body 30 is approximately coincident with an insertion direction of the insertion section 11 of the endoscope 4.

The insertion assisting device 20 causes the rotary body 30 to rotate in a state that the rotary body 30 comes in contact with an inner wall surface of the alimentary canal, and thereby the insertion assisting device 20 advances or retracts the insertion section 11 with use of friction force generated between the outer surface 30a of the rotary body 30 and the inner wall surface of the alimentary canal as the propulsive force. In order to move the insertion assisting device 20 in an advancing direction (insertion direction) shown by an arrow AV of FIG. 2, the outer surface 30a of the rotary body 30, which is located outside and comes in contact with the inner wall surface of the alimentary canal, is caused to move in a retracting direction (namely, in a direction reverse to the direction shown by the arrow AV). After moving in the retracting direction, the outer surface 30a located outside is bent by 180 degrees at a turning point of the rear end of the rotary body 30 and folded inward so as to be located inside. Then, after moving in the advancing direction, the outer surface 30a located inside is bent by 180 degrees at a turning point of the front end of the rotary body 30 and folded outward so as to be located outside. Accordingly, the insertion assisting device 20 causes the rotary body 30 to rotate in a state that the outer surface 30a thereof located outside moves in the retracting direction and the outer surface 30a thereof located inside moves in the advancing direction, and thereby the insertion assisting device 20 advances the insertion section 11 of the endoscope 4. In contrast, in order to move the insertion section 11 in the retracting direction, the rotary body 30 is caused to rotate in a direction reverse to the above, namely, in a state that the outer surface 30a thereof located outside moves in the advancing direction and the outer surface 30a thereof located inside moves in the retracting direction.

Figure 3:
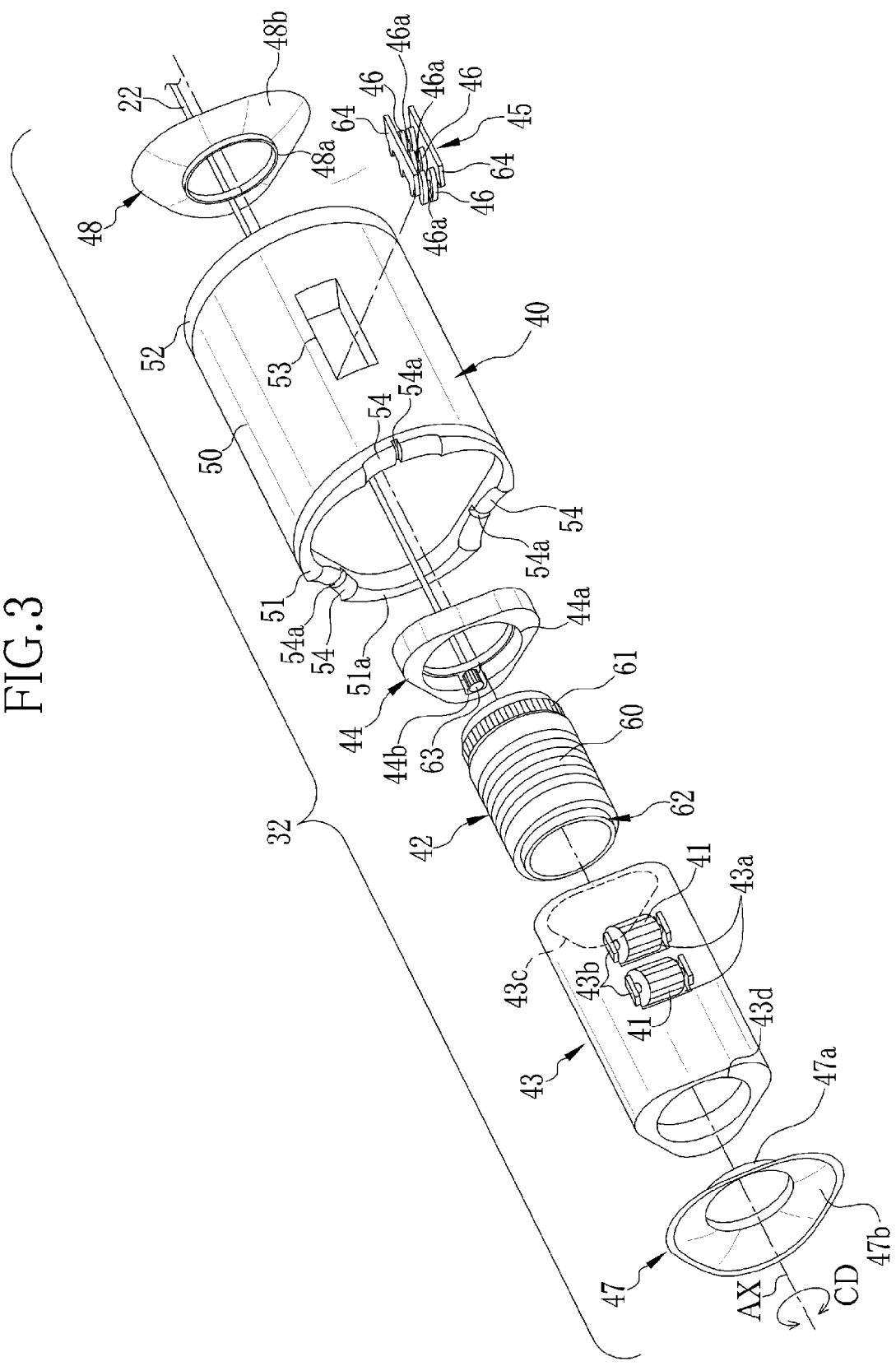
FIG. 3 is an exploded perspective view showing a structure of a support and drive part.

As shown in FIG. 3, the support and drive part 32 includes a supporting member 40 for supporting the rotary body 30 in a rotatable manner, a plurality of driving gears 41 for rotating the rotary body 30, a gear barrel (driving barrel) 42 for transmitting the driving force to each of the driving gears 41, and a holding member 43 for holding the gear barrel 42 in a rotatable manner. The support and drive part 32 further includes a lid member (hereinafter abbreviated as lid) 44 fixed to a rear end of the holding member 43, a roller unit 45 having a plurality of driven rollers 46 for pressing the rotary body 30 toward the driving gears 41, and first and second drawing-in preventing members 47 and 48 for preventing the inner wall surface of the body cavity from being drawn in the support and drive part 32.

The supporting member 40 has a cylindrical shape, in which the cross-sectional shape thereof in a direction orthogonal to the insertion axis AX has a circular shape on the outer peripheral surface, and has an approximately triangular shape (a shape such that each angle of an equilateral triangle is curved and rounded) on the inner peripheral surface. Further, the supporting member 40 has a main body 50 and contact protecting portions 51 and 52. The contact protecting portion 51 is attached to one end of the main body 50, and the contact protecting portion 52 is attached to the other end thereof. The main body 50 is made of metal such as aluminum and stainless. In contrast, each of the contact protecting portions 51 and 52 is made of a resin material having high slidability such as nylon, PEEK, and TEFLON (Trademark). Accordingly, it is possible to improve slidability at both front and rear ends of the supporting member 40 at which the rotary body 30 is folded, while keeping the strength of the supporting member 40.

The main body 50 has three openings 53. The openings 53 are arranged at intervals of 120 degrees in a circumferential direction CD so as to locate at flat portions of the approximately triangular inner peripheral surface of the main body 50, respectively. Further, each of the openings 53 is arranged at the vicinity of the center of the main body 50 in the insertion direction. The roller unit 45 is attached to each of the openings 53.

The contact protecting portions 51 which is attached to the front end of the main body 50 is provided with three concave portions 54 each of which is slightly depressed in comparison with the front end surface 51$a$. The concave portions 54 are arranged at intervals of 120 degrees in the circumferential direction CD so as to locate at the flat portions of the inner peripheral surface of the main body 50, respectively, as in the case of the openings 53. Each of the concave portions 54 is obtained by cutting out the front end surface 51$a$ in an approximately arc-like manner. Additionally, a groove 54$a$ depressed into an approximately rectangular shape is formed at the vicinity of the center of each of the concave portions 54.

Figure 4:
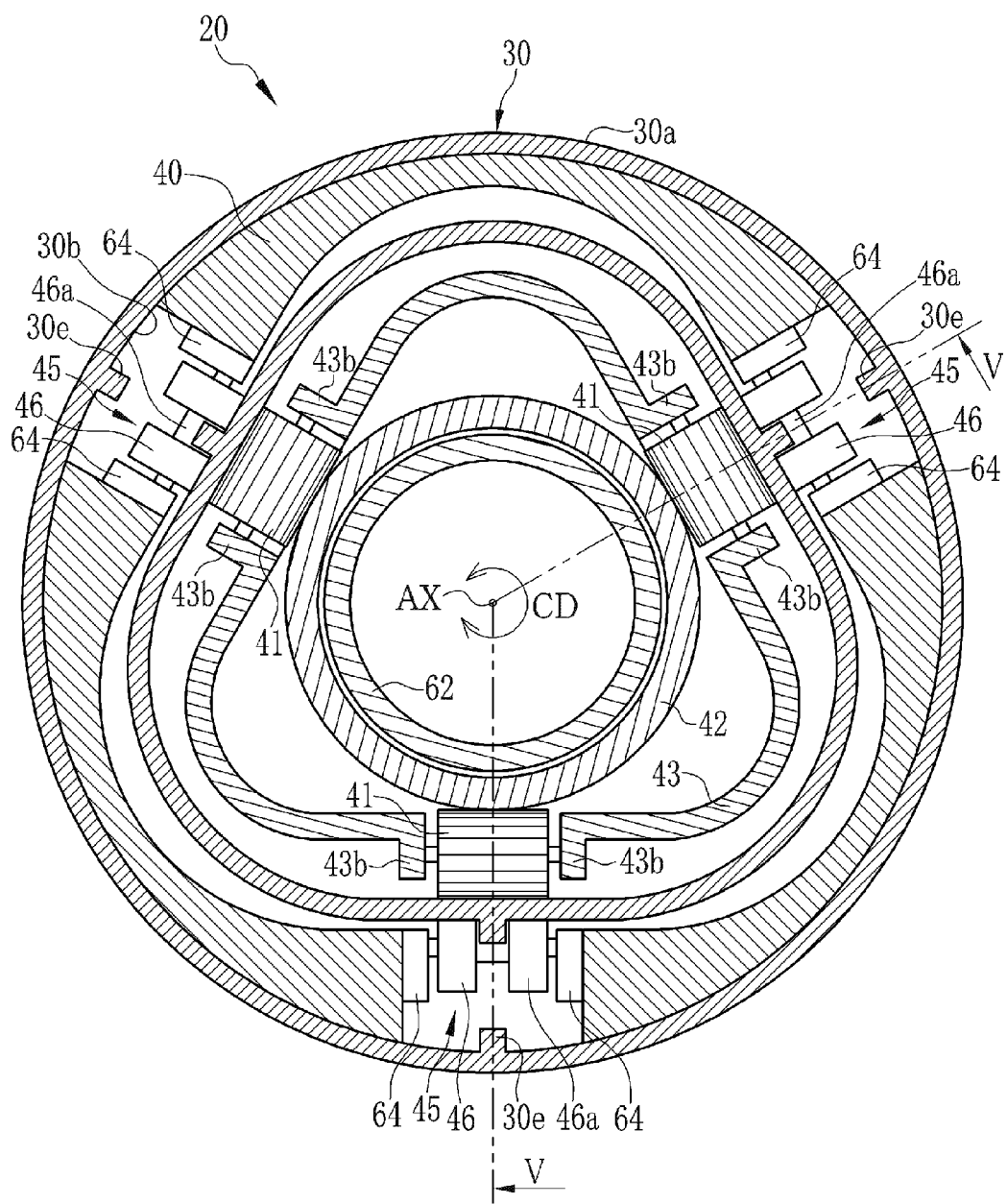
FIG. 4 is a cross-sectional view of the insertion assisting device in a direction orthogonal to an insertion direction.
Figure 5:
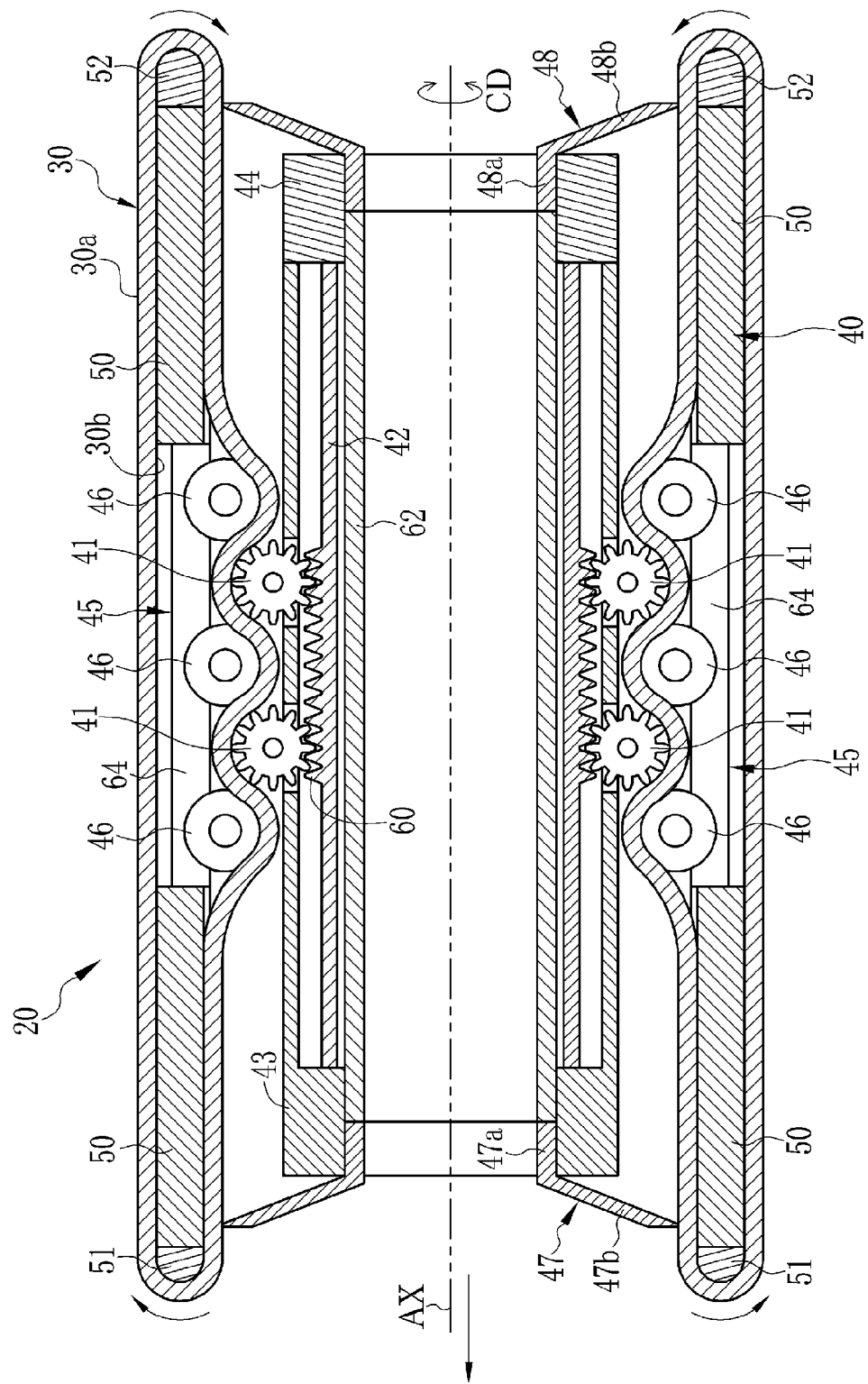
FIG. 5 is a cross-sectional view taken along lines V-V of FIG. 4.

As shown in FIGS. 4 and 5, the rotary body 30 is wound around the supporting member 40 so as to cover the supporting member 40 entirely. Since the supporting member 40 is located in a space defined by an inner surface 30$b$ of the rotary body 30 in the form of toroid, the supporting member 40 supports the rotary body 30 in a rotatable manner. Each of the driving gears 41, the gear barrel 42, the holding member 43, and the lid 44 are contained in the space inside the supporting member 40, so as to locate inside in comparison with the rotary body 30 rotating inside the supporting member 40.

The holding member 43 is shaped into a triangular cylindrical shape shorter than the supporting member 40 and has a cross-section slightly smaller than that of the inner peripheral surface of the supporting member 40. Two openings 43$a$ each having an approximately rectangular shape are formed in each side surface of the holding member 43. Each of the openings 43$a$ is positioned so as to face the opening 53 formed in each of the side surfaces of the supporting member 40 when the holding member 43 is incorporated into the supporting member 40. Additionally, four supports 43$b$ protruding approximately vertically are formed on each of the side surfaces of the holding member 43. Each of the supports 43$b$ is disposed adjacent to an edge of each of the openings 43$a$ and extends in a direction approximately orthogonal to the insertion axis AX.

Two driving gears 41 are provided to each of the side surfaces of the holding member 43, and namely, the total number of the driving gears 41 is six. Each of the driving gears 41 is located inside each of the openings 43$a$, and the rotating shaft of each of the driving gears 41 is supported by each of the support 43$b$. Thereby, each of the driving gears 41 rotates around the direction approximately orthogonal to the insertion axis AX. As described above, when the holding member 43 is incorporated into the supporting member 40, each of the openings 53 of the supporting member 40 faces the openings 43$a$ of the holding member 43. Accordingly, when the holding member 43 is incorporated into the supporting member 40, each of the driving gears 41 also faces the opening 53 of the supporting member 40.

The diameter of each of the driving gears 41 and the height of each of the supports 43$b$ are respectively adjusted such that the driving gear 41 partially enters in the holding member 43 through the opening 43$a$ and the driving gear 41 comes in contact with the outer surface 30$a$ of the rotary body 30 rotating inside the supporting member 40.

The gear barrel 42 has an approximately cylindrical shape. A worm 60 is provided on an outer surface of the gear barrel 42. A spur gear 61 having a plurality of teeth arranged in the circumferential direction is provided on a rear end of the gear barrel 42. The diameter of the worm 60 and the height of the teeth of the spur gear 61 are adjusted such that the worm 60 meshes with each driving gear 41 that has entered the inside of the holding member 43, in the state where the gear barrel 42 is supported by the holding member 43 and the lid 44. Accordingly, although the driving gear 41 is a worm wheel, the teeth height of the driving gear 41 is low so as not to damage the rotary body 30.

The teeth of each of the driving gears 41 correspond to a tilt (pitch) of the worm 60 formed spirally, and slightly tilt relative to the direction approximately orthogonal to the insertion axis AX. Accordingly, when the gear barrel 42 rotates around the insertion axis AX in the circumferential direction CD, the worm 60 meshes with each of the driving gears 41, and thereby each of the driving gears 41 rotates.

Further, the outer surface 30$a$ of the rotary body 30 is provided with three rack gear portions 30$c$ (see FIG. 2). Each of the rack gear portions 30$c$ has a plurality of gear grooves 30$d$ which are arranged along the rotational direction. The gear grooves 30$d$ mesh with the teeth of the driving gear 41. The rack gear portions 30$c$ are arranged at intervals of 120 degrees in the circumferential direction CD, so as to correspond to the driving gears 41 disposed in each of the side surfaces of the holding member 43, respectively. Each of the gear grooves 30$d$ slightly tilts relative to a direction approximately orthogonal to the rotational direction as in the cases of the worm 60 of the gear barrel 42 and the teeth of the driving gear 41. Since the teeth of each of the driving gears 41 mesh with each of the grooves 30$d$, each of the rack gear portions 30$c$ increases the transmitting efficiency of the driving force to the rotary body 30 in accordance with the rotation of each of the driving gears 41.

A shaft barrel 62 having an approximately cylindrical shape is inserted into the gear barrel 42. An external diameter of the shaft barrel 62 is substantially the same as or slightly smaller than an inner diameter of the gear barrel 42. The internal diameter of the shaft barrel 62 is almost the same as the diameter of the insertion section 11 of the endoscope 4. Accordingly, the shaft barrel 62 supports the gear barrel 42 in a rotatable manner, and constitutes the attachment portion 32$a$ which is attached to the supporting member 11. Further, the length of the shaft barrel 62 in the axial direction is longer than the gear barrel 42, such that both ends of the shaft barrel 62 protrude from the gear barrel 42. The gear barrel 42 is supported in a rotatable manner by the holding member 43 and the lid 44 at the both ends of the shaft barrel 62 protruding from the gear barrel 42.

A pinion gear (small gear) 63 coupled to the front portion of the torque wire 22 meshes with the spur gear 61 of the gear barrel 42. The pinion gear 63 is rotated by the torque wire 22 so as to transmit the driving force to the spur gear 61, and thereby causes the gear barrel 42 to rotate on the outer periphery of the shaft barrel 62.

The rear end of the holding member 43 has an opening 43c having an approximately triangular shape for introducing the gear barrel 42. The front end of the holding member 43 has an opening 43d having an approximately circular shape into which one end of the shaft barrel 62 is fitted. A diameter of the opening 43d is substantially equal to the outer diameter of the shaft barrel 62. Accordingly, one end of the shaft barrel 62 is fitted into the opening 43d, and the gear barrel 42 is held in a rotatable manner by the holding member 43.

The lid 44 has substantially the same shape as the front end portion of the holding member 43 having the opening 43d, and fixed to the rear end of the holding member 43. Further, the lid 44 has an approximately circular opening 44a into which the other end of the shaft barrel 62 is fitted. Accordingly, the gear barrel 42 is located between the holding member 43 and the lid 44, and rotatable around the shaft barrel 62. The worm 60 enters in the internal space of the holding member 43 and the spur gear 61 enters in the internal space of the lid 44.

The inner surface of the lid 44 has a recess 44b for housing the pinion gear 63. The recess 44b is formed such that the spur gear 61 entering in the internal space of the lid 44 meshes with the pinion gear 63 in a state that the gear barrel 42 is held in the rotatable manner between the holding member 43 and the lid 44. The torque wire 22 is coupled to the pinion gear 63 through a through hole (not shown in the drawing) formed in a surface of the recess 44b orthogonal to the insertion axis AX.

The roller unit 45 consists of three driven rollers 46 and a pair of supporting plates 64 for supporting the driven roller 46 from both sides in a rotatable manner. The roller unit 45 is inserted through an opening 53 from outside of the supporting member 40, and attached to the supporting member 40 in a state that each of the driven rollers 46 enters in the supporting member 40. Thus, the rotary body 30 is sandwiched between each of the driving gears 41 and each of the driven rollers 46. Each of the driven rollers 46 presses the rotary body 30 against each of the driving gears 41. Thus, the driving force in accordance with the rotation of each of the driving gears 41 is adequately transmitted to the rotary body 30.

When each of the driving gears 41 rotates in accordance with the rotation of the gear barrel 42, the rotary body 30 is sandwiched between each of the driving gears 41 and each of the driven rollers 46, each of the driven rollers 46 presses the rotary body 30 against each of the driving gears 41 to generate a frictional force, and the teeth of each of the driving gears 41 mesh with the gear groove 30d. Thereby, the driving force of each of the driving gears 41 is transmitted to the rotary body 30, and the rotary body 30 rotates. Note that, the rack gear portions 30c of the rotary body 30 are not necessarily provided, and the driving force may be transmitted to the rotary body 30 with use of friction force generated between each of the driving gears 41 and the outer surface 30a.

Further, as shown in FIG. 5, in a state that the number of the driven rollers 46 is larger by one than the number of the driving gears 41, the driving gears 41 and the driven rollers 46 are arranged at almost the same arrangement pitch, such that each of the driving gears 41 is located between the adjacent driven rollers 46 by being deviated by ½ pitch from the adjacent driven rollers 46 in the direction along the insertion axis AX. Further, the diameter and the arrangement pitch of the driving gears 41 and the driven rollers 46 are respectively adjusted such that each of the driving gears 41 and each of the driven rollers 46 sandwich the rotary body 30 therebetween while being partially overlapped with each other in the radial direction of the supporting member 40.

Consequently, the portion of the rotary body 30, which is sandwiched between each of the driving gears 41 and each of the driven rollers 46, is curved in a wave shape. When the rotary body 30 is curved as described above, a contact area of the rotary body 30 with each of the driving gears 41 is increased in comparison with the case where the rotary body 30 to be sandwiched between each of the driving gears 41 and each of the driven rollers 46 is in the straight-line form, and the contact pressure is made higher. Therefore, the driving force of each of the driving gears 41 can be more adequately transmitted to the rotary body 30.

When the rotary body 30 is sandwiched as described above, the movement of the holding member 43 in the direction along the insertion axis AX is limited by each of the driving gears 41 and each of the driven rollers 46 partially overlapped with each other in the radial direction. Therefore, the components incorporated into the supporting member 40 are prevented from being fallen from the supporting member 40.

The inner surface 30b of the rotary body 30 is provided with protrusions 30e protruding in a streaky manner along the rotational direction and having an approximately rectangular cross-section (see FIG. 4). Each of the protrusions 30e is provided so as to correspond to each of the driven rollers 46. The protrusions 30e are arranged at intervals of 120 degrees in the circumferential direction CD so as to face each of the rack gear portions 30c formed on the outer surface 30a. A groove (small-diameter portion) 46a, which engages with the protrusion 30e, is formed at the vicinity of the center of each of the driven rollers 46. In the case where each of the protrusions 30e and each of the grooves 46a are engaged with each other as described above, it is possible to prevent the rotary body 30 from being twisted and rotating abnormally. Note that, it is preferable that a lubricant is applied between the protrusion 30e and the groove 46a so as to increase slidability therebetween.

The first drawing-in preventing member 47 includes a fitting portion 47a in the form of ring which fits into the opening 43d of the holding member 43, and a drawing-in preventing portion 47b having a mortar shape whose diameter increases as the distance from the fitting portion 47a increases. The first drawing-in preventing member 47 is made of a resin material having elasticity.

The outer diameter of the fitting portion 47a is substantially equal to the diameter of the opening 43d of the holding member 43. Thereby, the fitting portion 47a is fitted into the opening 43d, and the first drawing-in preventing member 47 is held by the holding member 43. The drawing-in preventing portion 47b is formed to have a mortar shape with an approximately triangular cross-section similar to the cross-section of the holding member 43 or the like. Further, the cross-section of an end portion of the drawing-in preventing portion 47b is slightly larger than the cross-section of the holding member 43.

In FIG. 5, the gear barrel 42, the holding member 43, and the lid 44 are joined together at their end surfaces, and the total length of them is shorter than the length of the supporting member 40 in the axial direction. Further, the front portion of the drawing-in preventing portion 47b is located inward of the front end of the supporting member 40 in a state that the first drawing-in preventing member 47 is fixed to the holding member 43.

Consequently, the front portion of the drawing-in preventing portion 47b of the first drawing-in preventing member 47 comes in contact with the outer surface 30a of the rotary body 30 which moves inside the supporting member 40, such that the drawing-in preventing portion 47b blocks the space formed between the rotary body 30 and the holding member 43. Since the drawing-in preventing portion 47b of the first drawing-in preventing member 47 blocks the space in a state that the drawing-in preventing portion 47b elastically deforms, it is possible to prevent the inner wall surface of the body cavity from being drawn in the space formed between the rotary body 30 and the holding member 43.

The second drawing-in preventing member 48 includes a fitting portion 48a in the form of ring which fits into the opening 44a of the lid 44, and a drawing-in preventing portion 48b having a mortar shape whose diameter increases as the distance from the fitting portion 48a increases, as in the case of the first drawing-in preventing member 47. As the structure of the second drawing-in preventing member 48 is the same as that of the first drawing-in preventing member 47, the detailed description thereof will be omitted. Additionally, the second drawing-in preventing member 48 has a through-hole (not shown in the drawing) through which the torque wire 22 is inserted.

Figure 6:
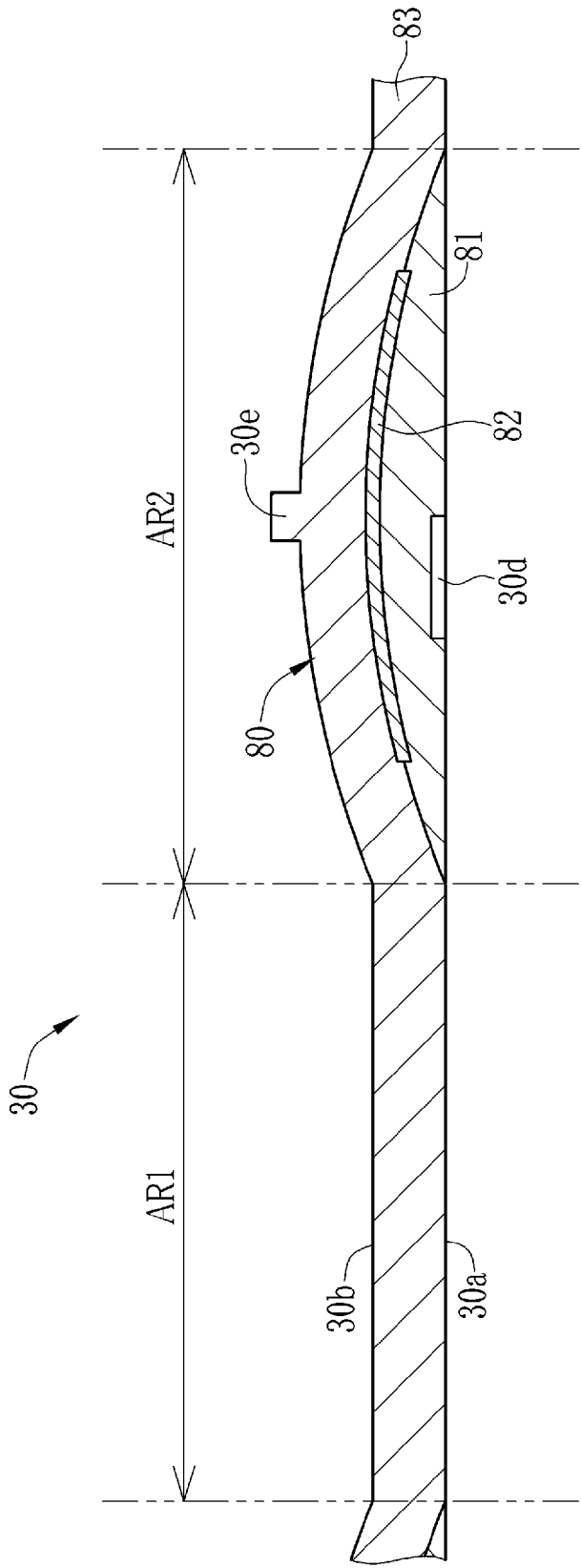
FIG. 6 is a partial cross-sectional view of a rotary body in a direction approximately orthogonal to a rotational direction.

As shown in FIG. 6, the rotary body 30 includes a first area AR1 continuously formed to have an approximately fixed thickness along the rotational direction, and a second area AR2 continuously formed to have a convex portion 80 projected in an arc-like manner along the rotational direction. The strength of the second area AR2 is made to be higher than that of the first area AR1 thanks to the convex portion 80 having the increased thickness. The second area AR2 comes in contact with each of the driving gears 41 and each of the driven rollers 46, and receives the driving force therefrom. The number of the first areas AR1 and the number of the second areas AR2 provided to the rotary body 30 are respectively three, and the first areas AR1 and the second areas AR2 are alternately arranged in the circumferential direction CD.

Since the first areas AR1 and the second areas AR2 having the increased thickness are provided to the rotary body 30 as described above, it is possible to keep a balance between the strength necessary for driving the rotary body 30 and flexibility necessary for the smooth rotation of the rotary body 30. Note that the width of each of the areas AR1 and AR2 may be arbitrarily selected in accordance with the width of each of the driving gears 41 and the driven rollers 46 and the diameter of the supporting member 40.

The inner surface 30b is provided with the convex portions 80. In contrast, on the outer surface 30a which comes in contact with the inner wall surface of the body cavity, the first and second areas AR1 and AR2 are on the same plane. The convex portion 80 is formed into a circular arc whose central portion in the rotational direction is swollen. When the convex portion 80 is viewed in a cross-section along a direction substantially orthogonal to the rotational direction, the central portion is the thickest, and the thickness gradually gets thinner toward both side ends. Thereby, the first areas AR1 and the second areas AR2 can be joined to each other smoothly. Additionally, the rack gear portion 30c is formed at the vicinity of the center of the outer surface 30a of the second area AR2, and the protrusion 30e is provided at the vicinity of the central top of the convex portion 80 which constitutes part of the inner surface 30b.

Figure 7:
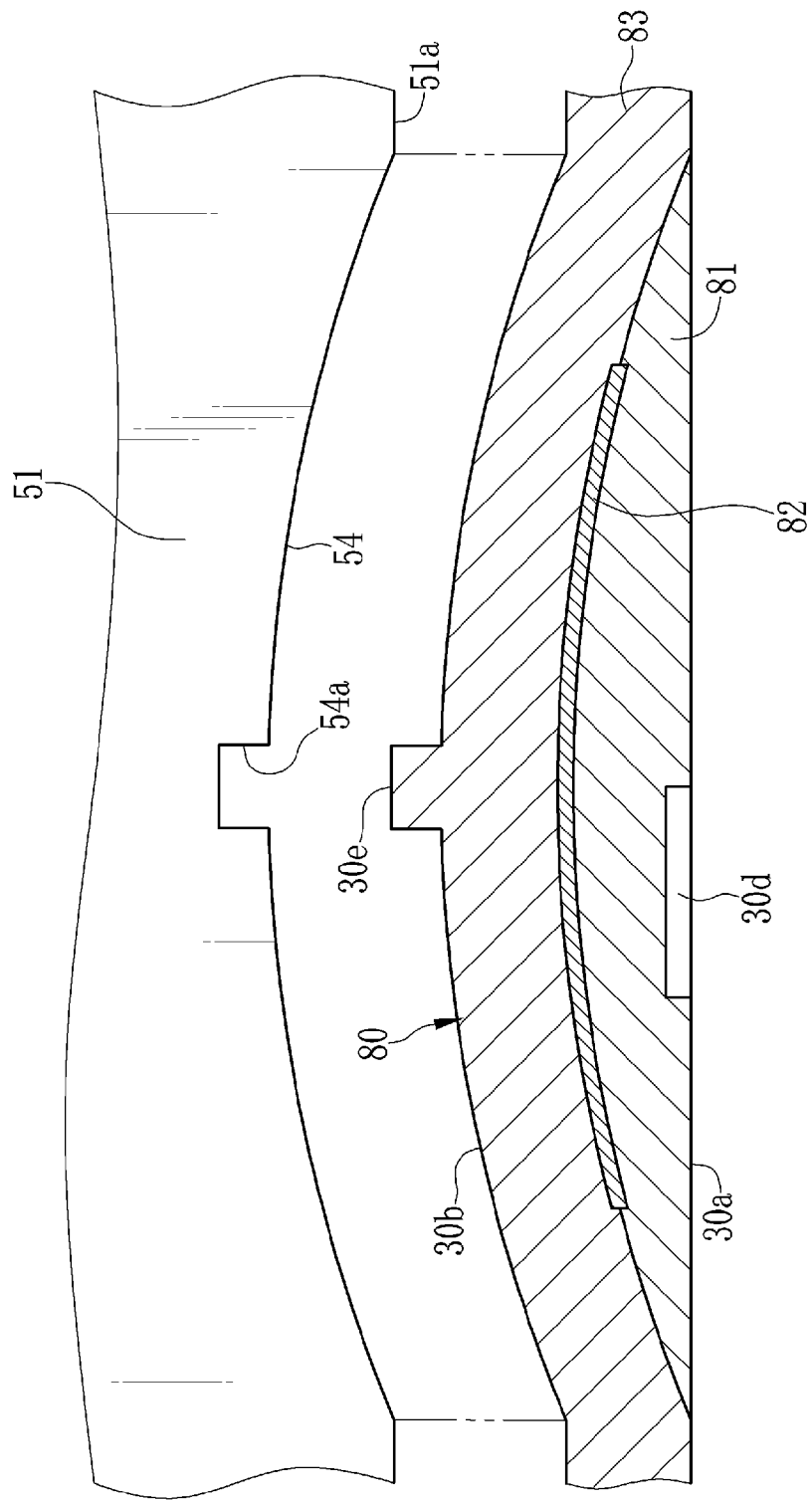
FIG. 7 is an explanatory view showing a structure of a convex portion of the rotary body and a structure of a concave portion of a supporting member.

As shown in FIG. 7, the concave portion 54 formed on the front end surface 51a of the contact protecting portion 51 of the supporting member 40 is depressed so as to correspond to the convex portion 80, and guides the convex portion 80. Additionally, the protrusion 30e enters into the groove 54a formed at the vicinity of the center of each of the concave portions 54.

Accordingly, when the inner surface 30b of the rotary body 30 comes in contact with the front end surface 51a of the supporting member 40, the first area AR1 and the front end surface 51a are attached firmly to each other, and the convex portion 80 is fitted into the concave portion 54. Thus, there is not a difference in height between the first area AR1 and the second area AR2 on the outer surface 30a, and the first area AR1 and the second area AR2 lie on the same plane.

Even when the inner surface 30b of the rotary body 30 comes in contact with the front end surface 51a of the supporting member 40 as described above, the rotary body 30 does not come in point contact with the supporting member 40 at the second area AR2 having the increased thickness. Accordingly, it is possible to prevent the rotary body 30 from stopping rotating due to the pressure concentration caused by the point contact.

As shown in FIGS. 6 and 7, the second area AR2 of the rotary body 30 consists of a first layer 81 formed of polyurethane, a second layer 82 formed of a nylon mesh sheet, and a third layer 83 formed of polyurethane similarly to the first layer 81. Namely, the second area AR2 consists of a three-layer structure in which the second layer 82 for enhancing the strength is sandwiched between the first layer 81 and the third layer 83. In contrast, the first area AR1 consists of a single-layer structure including the third layer 83 only.

The nylon mesh sheet is obtained by arranging nylon fibers in a square lattice pattern, and has a low flexural modulus and a high tensile modulus. Therefore, the nylon mesh is easily bent, but is not easily stretched. Consequently, the second layer 82 prevents the first layer 81 and the third layer 83 from being stretched in the rotational direction. Note that, the second layer 82 is not limited to the nylon, and may be a mesh sheet made of other materials as long as it is easily bent, but is not easily stretched.

It is necessary to use a material which has flexibility and biocompatibility to form the rotary body 30. As such a material, biocompatible plastic having bendability and flexibility such as polyurethane is preferably used because it is relatively inexpensive. However, the biocompatible plastic is also flexible in a stretching direction. Therefore, if the rotary body 30 is formed of the biocompatible plastic only, there is fear that the rotary body 30 may be stretched in the rotational direction and propulsive force may be decreased at the time of transmitting the driving force by the driving gears 41 and at the time of propelling the insertion assisting device 20 with use of friction against the inner wall surface of the body cavity. Further, if the rotary body 30 is formed of only a rigid material which is hardly stretched, the load applied at the time of folding (turning) the rotary body 30 at the front and rear ends of the supporting member 40 is increased, and therefore the rotary body 30 does not rotate smoothly. As a result, the propulsive force is also decreased.

In contrast, when the second area AR2 of the rotary body 30 consists of the three-layer structure including the first and third layers 81 and 83 made of flexible polyurethane and the second layer 82 made of nylon mesh sheet which is easily bent, but is not easily stretched as described above, the rotary body 30 is not stretched in the rotational direction even if being applied with force, and the rotary body 30 can be rotated smoothly. Thereby, it is possible to prevent decrease in the propulsive force.

Furthermore, if the first area AR1 to which the driving force is not directly applied consists of a single-layer structure including only the third layer 83 so as to permit the first area AR1 to be stretched in the rotational direction, the load applied at the time of folding the rotary body 30 at both ends of the supporting member 40 is decreased, and therefore the rotary body 30 can be rotated more smoothly. Accordingly, the second area AR2 is thicker than the first area AR1 so as to improve the strength thereof, and is not easily stretched in the rotational direction in comparison with the first area AR1. Note that the material for forming the first and third layers 81 and 83 is not limited to polyurethane, and may be polyvinyl chloride, polyamide resin, fluororesin, and other biocompatible plastics.

Further, since the first layer 81 made of flexible polyurethane is made in contact with the driving gear 41, the teeth of the driving gear 41 enter in the first layer 81, and the friction coefficient between the first layer 81 and the driving gear 41 is increased. Therefore, it is possible to prevent decrease in the propulsive force caused by slippage (idle rotation) of the driving gear 41.

By the way, the inner surface 30b of the rotary body 30 fundamentally does not come in contact with the inner wall surface of the body cavity. Therefore, in the case where the protrusion 30e is not provided, only the first layer 81 and the second layer 82 may be used such that the first area AR1 consists of a single-layer structure including only the first layer 81, and the second area AR2 consists of a two-layer structure including the first and second layers 81 and 82 in which the exposed surface of the second layer 82 is the inner surface 30b.

Figure 8:
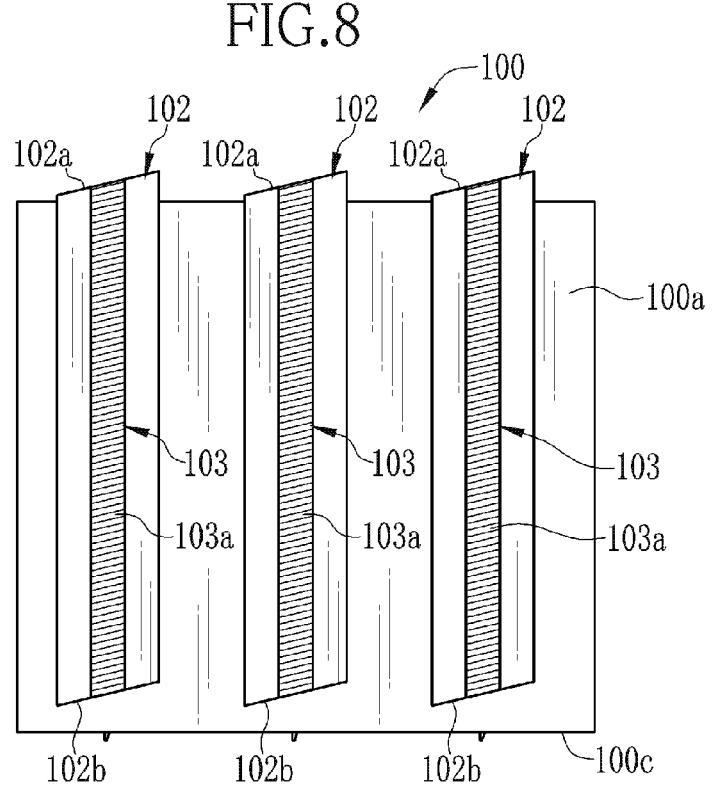
FIG. 8 is a plan view of a rotary body forming sheet.
Figure 9:
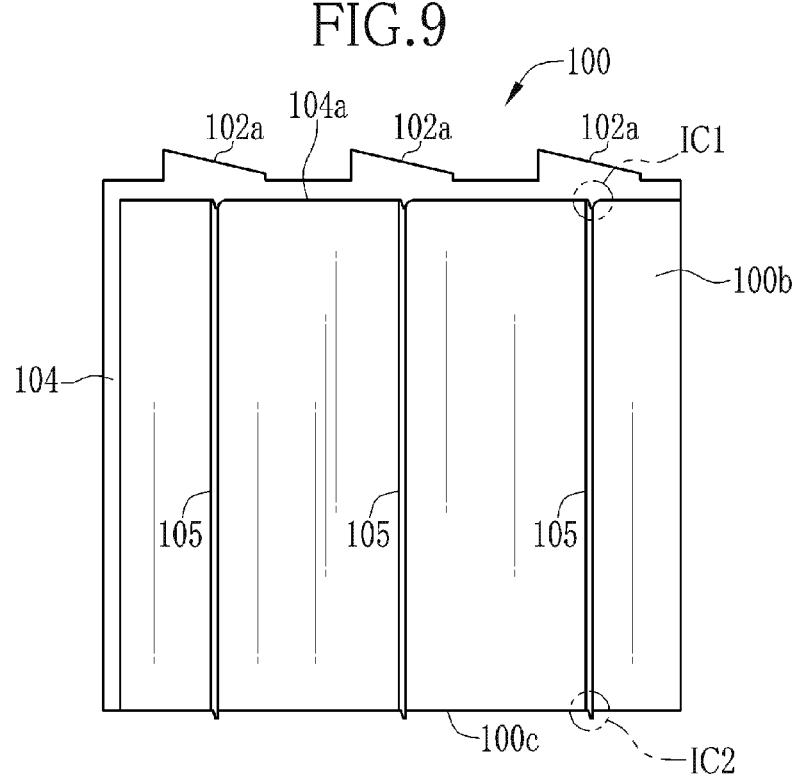
FIG. 9 is a rear view of the rotary body forming sheet.

In FIGS. 8 and 9, a rotary body forming sheet 100 is produced as an exploded state of the rotary body 30 in view of productivity and assemblability of the rotary body 30. The rotary body forming sheet 100 is an approximately rectangular sheet. The length and width of the rotary body forming sheet 100 are appropriately adjusted, such that the rotary body forming sheet 100 can be wound over the supporting member 40.

Side ends of the rotary body forming sheet 100 are adhered or welded to each other, and thereby the rotary body forming sheet 100 is formed into a cylindrical shape. The cylindrical rotary body forming sheet 100 is incorporated together with other components at the time of assembling the support and drive part 32. After the support and drive part 32 is assembled, the rotary body forming sheet 100 is folded so as to be turned back at the both ends of the supporting member 40. Then, the front end and the rear end of the rotary body forming sheet 100 are adhered or welded to each other, and thereby the rotary body forming sheet 100 is formed into a toroid shape in a state that the supporting member 40 is wrapped with the rotary body forming sheet 100. Accordingly, the rotary body forming sheet 100 is formed into the rotary body 30.

As shown in FIG. 8, a front surface 100a of the rotary body forming sheet 100 is provided with three reinforcing portions 102 which are made thicker so as to have increased strength. Each of the reinforcing portions 102 is formed into an approximately elongated parallelogram. The reinforcing portions 102 are arranged at a predetermined interval in a direction substantially orthogonal to the longitudinal direction thereof. Namely, the longitudinal direction of the reinforcing portion 102 (the vertical direction in the drawing) corresponds to the rotational direction of the rotary body 30. The reinforcing portions 102 constitute the second areas AR2 of the rotary body 30, and portions between the reinforcing portions 102 constitute the first areas AR1 of the rotary body 30.

Each of the reinforcing portions 102 has a rack gear portion 103 corresponding to the rack gear portion 30c of the rotary body 30 after the rotary body forming sheet 100 is formed into the rotary body 30. The front surface 100a of the rotary body forming sheet 100 becomes the outer surface 30a of the rotary body 30.

A gear groove 103a of each of the rack gear portions 103 is formed so as to correspond to the worm 60 of the gear barrel 42 and the teeth of the driving gear 41, and slightly tilt relative to the direction substantially orthogonal to the longitudinal direction thereof. Additionally, a front end 102a and a rear end 102b of the reinforcing portion 102, at which the ends of the rack gear portion 103 are exposed, are formed to be slightly tilt relative to the direction substantially orthogonal to the longitudinal direction thereof at the same angle as that of the gear groove 103a.

The front end 102a and the rear end 102b of the reinforcing portion 102 are spliced to each other, when the front end and the rear end of the rotary body forming sheet 100 are adhered or welded to each other such that the rotary body forming sheet 100 is formed into the toroid shape. The both ends of the rack gear portion 103 respectively exposed at the front end 102a and the rear end 102b of the reinforcing portion 102 are formed to have an adjusted distance such that deviation of pitch does not occur at the splicing portion of the front and rear ends 102a and 102b after the rack gear portion 103 becomes the annular rack gear portion 30c of the rotary body 30.

If each of the front and rear ends 102a and 102b is formed along the direction substantially orthogonal to the longitudinal direction thereof, each of the ends 102a and 102b obliquely transverses the gear groove 103a. Therefore, deviation of pitch and difference in height are more easily generated at the gear groove 103a at the splicing portion in accordance with the positional deviation in a transverse direction. Such deviation of pitch and difference in height cause trouble in the mesh with the driving gear 41, and result in driving defect of the rotary body 30. In contrast, when each of the front and rear ends 102a and 120b is cut approximately in parallel with the formation direction of the gear groove 103a as described above, even if positional deviation in a transverse direction occurs, it is possible to prevent generation of deviation of pitch and difference in height in the gear groove 103a at the splicing portion.

In FIG. 9, a stepped portion 104 lower by one step than peripheral portions is provided to a rear surface 100b of the rotary body forming sheet 100. The stepped portion 104 is formed into an approximately "L" shape extending from the front end of the rotary body forming sheet 100 to one of the side ends thereof. The stepped portion 104 functions as a splicing portion for adhering or welding the front end of the rotary body forming sheet 100 to the rear end thereof, and adhering or welding the side ends of the rotary body forming sheet 100 to each other. At the time of forming the rotary body 30, the stepped portion 104 is laid on the opposite end, and adhesion or welding is performed on the overlapped portion.

An edge portion 104a at the front end of the stepped portion 104 is formed along the direction substantially orthogonal to the longitudinal direction of the rotary body forming sheet 100. The shape of a portion extending from the edge portion 104a of the stepped portion 104 to the front ends 102a of the reinforcing portion 102 is approximately the same as the shape of a portion extending from an edge portion 100c at the rear end of the rotary body forming sheet 100 to the rear ends 102b of the reinforcing portion 102. Note that, they are line-symmetrical with each other with respect to the longitudinal direction in accordance with inversion of front and rear surfaces.

The front end of the stepped portion 104 is laid on the rear end of the front surface 100a having no reinforcing portions 102, and adhered or welded thereto, and thereby the front end 102a and the rear end 102b of the reinforcing portion 102 are spliced to each other, and the edge portion 100c and the edge portion 104a are also spliced to each other. As a result, it is possible to form the rotary body 30 in which the overall thickness including the splicing portions is uniform and each of the outer surface 30a and the inner surface 30b is a flat surface without difference in height.

A rear surface 100b of the rotary body forming sheet 100 is provided with protrusions 105 corresponding to the protrusions 30e of the rotary body 30 after the rotary body 30 is formed. The protrusion 105 is formed into a rib shape having an approximately rectangular cross-section and protrudes in a streaky manner along the longitudinal direction.

Figure 10:
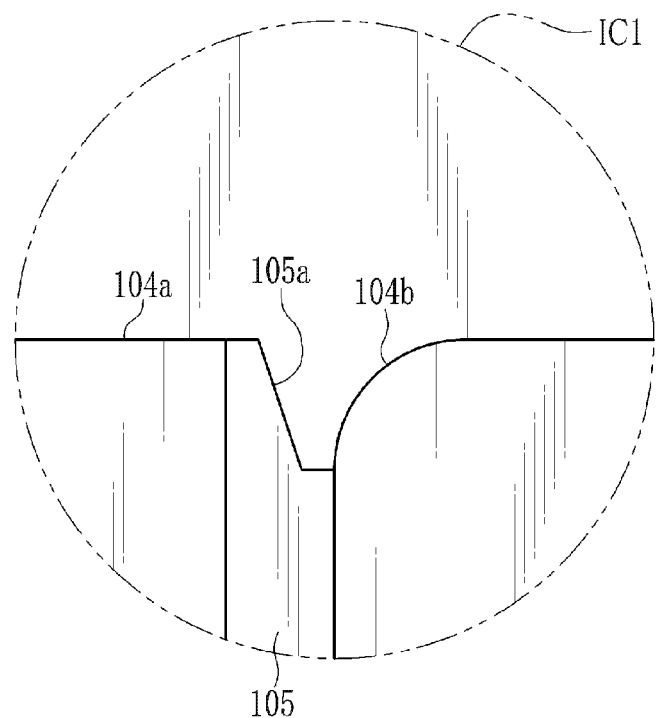
FIG. 10 is a partial enlarged view showing a structure of one end of a protrusion of the rotary body.

As shown in FIGS. 9 and 10, one end of the protrusion 105 surrounded by an imaginary circle IC1 is obliquely cut out to form a concavity 105a. Additionally, a cutout 104b for exposing the concavity 105a is formed at the edge portion 104a.

Figure 11:
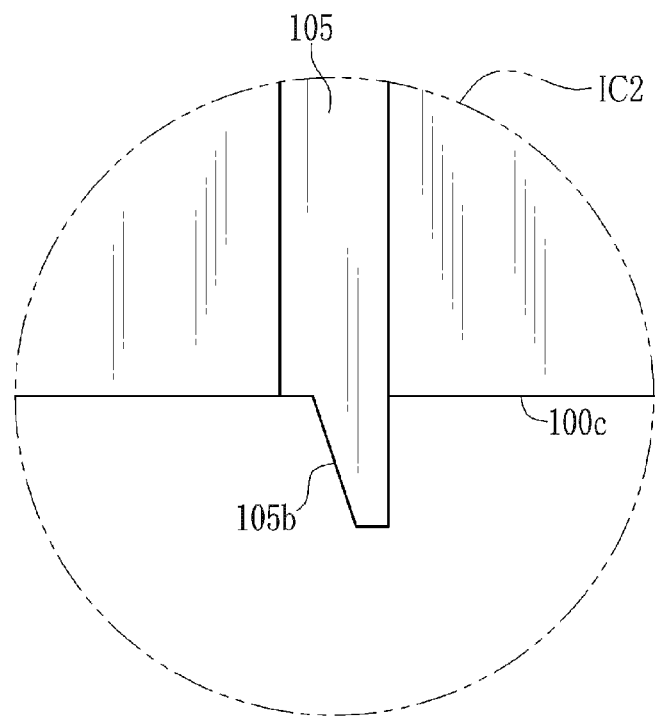
FIG. 11 is a partial enlarged view showing a structure of the other end of the protrusion of the rotary body.

As shown in FIGS. 9 and 11, the other end of the protrusion 105 surrounded by an imaginary circle IC2 is provided with a convexity 105b corresponding to the shape of the concavity 105a. The convexity 105b is formed so as to protrude from the edge portion 100c. When the edge portion 100c and the edge portion 104a are spliced to each other, the convexity 105b enters in the cutout 104b and is combined with the concavity 105a.

Consequently, when the front end and the rear end of the rotary body forming sheet 100 are adhered or welded to each other, the concavity 105a and the convexity 105b are made to be continuous with each other, and thus the annular protrusion 30e of the rotary body 30 formed. Further, since the concavity 105a and the convexity 105b are combined with each other as described above, it is possible to facilitate the positioning of the both ends of the protrusion 105. Furthermore, since the contact area is increased, the strength of the adhesion or welding at the splicing portions can be also increased. Note that the imaginary circles IC1 and IC2 are auxiliary circles for indicating the areas to be displayed in an enlarged manner for the sake of convenience in the drawings. Therefore, the imaginary circles IC1 and IC2 are not actually provided to the rotary body forming sheet 100.

Figure 12:
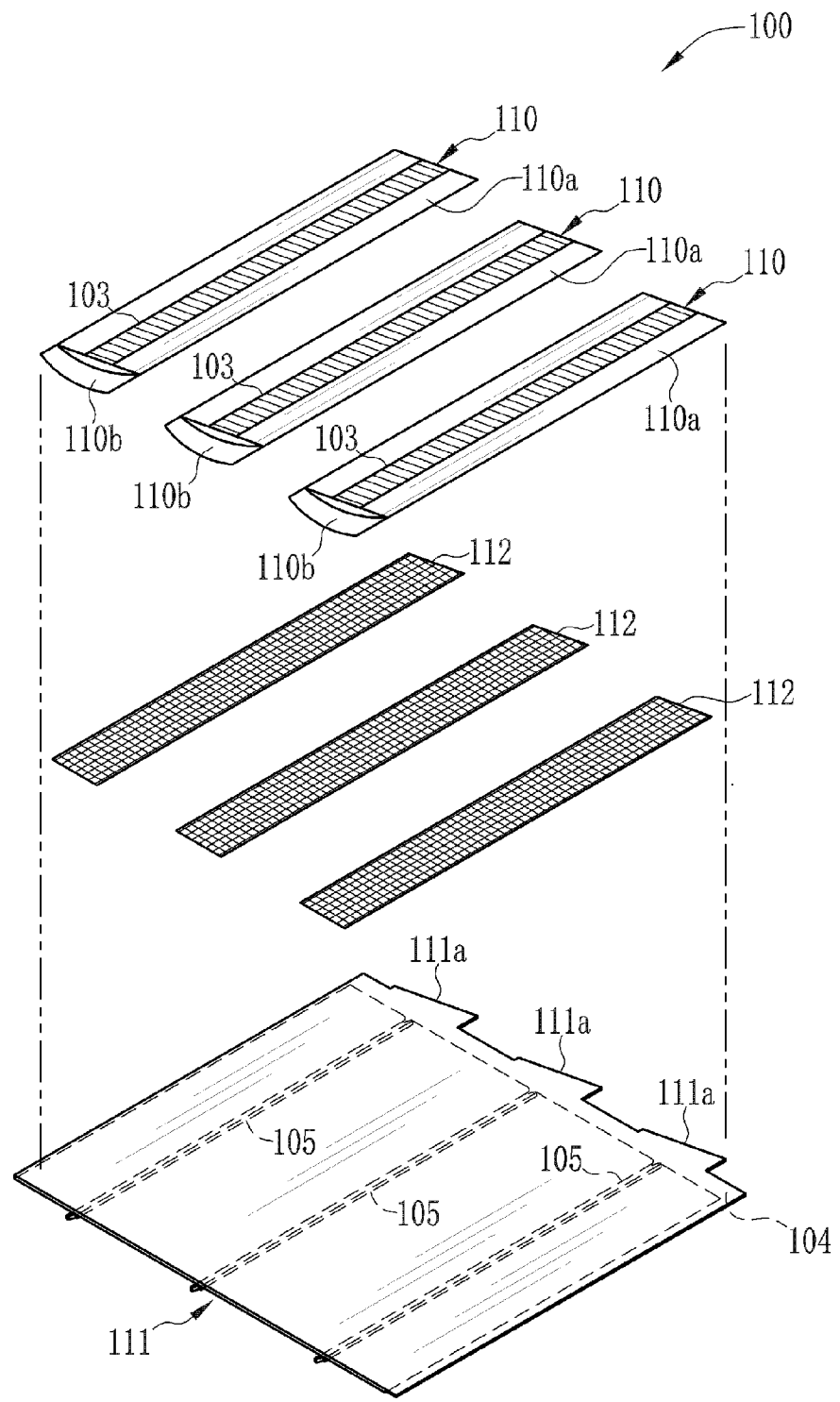
FIG. 12 is an exploded perspective view showing the structure of the rotary body forming sheet.

As shown in FIG. 12, the rotary body forming sheet 100 consists of three reinforcing portion forming sheets 110 for forming the reinforcing portions 102, a rear surface forming sheet 111 for forming the rear surface 100b, and three nylon mesh sheets 112 for forming the portion corresponding to the second layer 82 of the rotary body 30. These sheets 110 to 112 are overlapped and adhered or welded to each other so as to constitute a layer structure.

The reinforcing portion forming sheets 110 and the rear surface forming sheet 111 are made of polyurethane. Accordingly, when the sheets 110 to 112 are overlapped and adhered or welded to each other, the reinforcing portion forming sheet 110 is formed into the portion corresponding to the first layer 81 of the rotary body 30, and the rear surface forming sheet 111 is formed into a portion corresponding to the third layer 83 of the rotary body 30.

Each of the reinforcing portion forming sheets 110 has a main body part 110a having a shape of approximately parallelogram corresponding to the shape of the reinforcing portion 102, and a protection part 110b provided at one end of the main body part 110a. The rack gear portion 103 is formed on one of the surfaces of the main body part 110a. The other one of the surfaces of the main body part 110a is formed into a cylindrical surface shape whose central portion is swollen along the longitudinal direction.

The protection part 110b is formed into an extremely thin sheet which is continuous from the cylindrical surface of the main body part 110a. Further, the protection part 110b is formed to have a shape corresponding to the shape extending from the rear ends 102b of the rotary body forming sheet 100 to the edge portion 100c thereof. When the sheets 110 to 112 are overlapped and adhered or welded to each other, the protection part 110b covers the portion of the nylon mesh sheet 112 at a rear side with respect to the main body part 110a, and protects the nylon mesh sheet 112 such that the nylon mesh sheet 112 is not exposed outside.

The rear surface forming sheet 111 has a shape approximately equivalent to a profile of the rotary body forming sheet 100. Three trapezoidal projecting parts 111a corresponding to the reinforcing portions 102 of the rotary body forming sheet 100 are provided to the front end of the rear surface forming sheet 111. Additionally, the stepped portion 104 and the protrusions 105 are provided to one of the surfaces of the rear surface forming sheet 111.

Each of the nylon mesh sheets 112 is an approximately trapezoidal sheet having a width decreased in the direction orthogonal to the longitudinal direction of the reinforcing portion forming sheet 110. The nylon mesh sheet 112 has a low flexural modulus and a high tensile modulus. Namely, the nylon mesh sheet 112 is easily bent, but is not easily stretched. Further, the horizontal and vertical directions of the mesh formed in a square lattice pattern of the nylon mesh sheet 112 are substantially parallel to the longitudinal direction of the reinforcing portion forming sheet 110 and the direction orthogonal to the longitudinal direction thereof, respectively.

If the direction of the mesh of the nylon mesh sheet 112 is oblique to the longitudinal direction, the nylon mesh sheet 112 is stretched due to the deformation of the mesh. In contrast, if the direction of the mesh of the nylon mesh sheet 112 is substantially parallel to the longitudinal direction, the fibers are stretched straight, and therefore it is possible to more adequately prevent the rotary body 30 from being stretched in the rotational direction after the rotary body 30 is formed.

In order to produce the rotary body forming sheet 100, at first, each of the nylon mesh sheets 112 is disposed at a position corresponding to each of the projecting parts 111a on the surface of the rear surface forming sheet 111 on which the stepped portion 104 and the protrusions 105 are not provided. Thereafter, each of the reinforcing portion forming sheets 110 is disposed on the rear surface forming sheet 111 such that the end of each of the projecting parts 111a is set to the end of each of the reinforcing portion forming sheets 110 on a one-on-one basis.

The sheets 110 to 112 are adhered or welded to each other in a state that the position of each of the sheets 110 to 112 is set as described above, so as to produce the rotary body forming sheet 100. At this time, the surface of the reinforcing portion forming sheet 110 on which the rack gear portion 103 is formed and the front surface of the rear surface forming sheet 111 are made to be on the same plane. Thereby, the convex pattern of the reinforcing portion forming sheet 110 is transferred to the rear surface 100b, and thereby the convex portion 80 is formed on the rear surface 100b.

Note that when the sheets 110 to 112 are adhered or welded to each other as described above, there is generated difference in height between the protection part 110b of the reinforcing portion forming sheet 110 and the front surface of the rear surface forming sheet 111. Since the difference in height results in thickness unevenness, the protection part 110b is preferably melted so as to remove the difference in height at the time of adhering or welding the sheets 110 to 112 to each other, for the purpose of removing the thickness unevenness.

At the time of assembling the insertion assisting device 20, at first, the gear barrel 42 is held by the holding member 43 and the lid 44, and the lid 44 is fixed to the rear end of the holding member 43 with use of screws, so as to integrate them together. Thereafter, the rotary body forming sheet 100 is rolled up in a state that the front surface 100a is located inside, and the side end of the stepped portion 104 is laid on the opposite side end, and adhesion or welding is performed on the overlapped portion. Thereby, the rotary body forming sheet 100 is formed into a cylindrical shape.

After the rotary body forming sheet 100 is formed into a cylindrical shape, positioning is performed such that each of the driving gears 41 and the gear groove 103a of each of the rack gear portions 103 are meshed with each other, and then the holding member 43, the lid 44, and the gear barrel 42 held by them are inserted into the inside of the rotary body forming sheet 100. Thereafter, the members are inserted into the inside of the supporting member 40 such that each of the openings 53 faces the corresponding driving gears 41. Note that, the position of the rotary body forming sheet 100 in the longitudinal direction thereof is adjusted, such that both ends of the rotary body forming sheet 100 are exposed outside of the supporting member 40, upon being inserted into the supporting member 40.

After the holding member 43 and the lid 44 which hold the gear barrel 42, and the rotary body forming sheet 100 are inserted into the supporting member 40, the roller unit 45 is attached to a position corresponding to each of the openings 53, such that each of the driving gears 41 and each of the driven rollers 46 sandwich the rotary body forming sheet 100 therebetween, and such that the holding member 43 and the like are prevented from being fallen from the supporting member 40 with use of each of the driving gears 41 and each of the driven rollers 46 overlapped with each other in the radial direction.

After the roller unit 45 is attached and each of the members is held by the supporting member 40, the rotary body forming sheet 100 is folded at the front and rear ends of the supporting member 40, and the front and rear ends of the rotary body forming sheet 100 are adhered or welded to each other in a state that the front end of the stepped portion 104 is overlapped with the opposite end. Thereby, the rotary body 30 is obtained.

Thereafter, the fitting portion 47a of the first drawing-in preventing member 47 is fitted into the opening 43c of the holding member 43 such that the first drawing-in preventing member 47 is held by the holding member 43. Further, the fitting portion 48a of the second drawing-in preventing member 48 is fitted into the opening 44a of the lid 44 such that the second drawing-in preventing member 48 is held by the lid 44.

When the assembling of the insertion assisting device 20 is completed as described above, a continuous through-hole extending from the fitting portion 47a of the first drawing-in preventing member 47 to the fitting portion 48a of the second drawing-in preventing member 48 through the opening 43c of the holding member 43, the inner surface of the shaft barrel 62, and the opening 44a of the lid 44 is formed. The through-hole functions as the attachment portion 32a.

Next, an operation of the endoscope system 2 configured as described above will be hereinafter described. In the case of inspecting inside of the body cavity of the test subject with use of the endoscope system 2, at first, the overtube 23 through which the torque wire 22 is inserted is fitted onto the insertion section 11 of the endoscope 4, and the overtube 23 is attached to the insertion section 11. Thereafter, the distal portion 11a of the insertion section 11 is fitted into the attachment portion 32a of the support and drive part 32, and the insertion assisting device 20 is attached to the distal portion 11a.

After the insertion assisting device 20 and the overtube 23 are attached to the insertion section 11, the torque wire 22 is connected to the drive control device 21, and the universal cord 13 of the endoscope 4 is connected to the processor device and the light source device, and then interconnection between the components is adequately conducted so as to constitute the endoscope system 2. Then, the processor device, the light source device, and the drive control device 21 are powered on, to complete the preparation for inspection. Thereafter, the insertion section 11 of the endoscope 4 is inserted into the alimentary canal of the test subject, to start inspection.

When the distal portion 11a is advanced to a predetermined position in the alimentary canal, for example, just before the sigmoid colon, the forward button 26a provided in the manipulation unit 26 of the drive control device 21 is operated to input instruction for advancing the insertion assisting device 20 to the controller 25. Upon receiving the instruction for advancing the insertion assisting device 20, the controller 25 drives the motor 24 to rotate in the advancing direction at the speed in accordance with the instruction from the speed setting dial 26d.

When the motor 24 rotates, the driving force is transmitted through the torque wire 22 and the pinion gear 63 to the gear barrel 42. In accordance with the rotation of the gear barrel 42, each of the driving gears 41 rotates. Upon rotation of each of the driving gears 41, the driving force of each of the driving gears 41 is transmitted to the rotary body 30 sandwiched between the driving gears 41 and the driven rollers 46, and thereby the rotary body 30 rotates.

At this time, since the rotary body 30 is provided with the first area AR1 and the second area AR2, and the driving force is transmitted to the rotary body 30 through the second area AR2 which has strength higher than that of the first area AR1, the driving force is adequately transmitted to the rotary body 30, and the first area AR1 is flexibly deformed, such that the rotary body 30 smoothly rotates. Further, the second area AR2 of the rotary body 30 consists of the three-layer structure including the first and third layers 81 and 83 made of flexible polyurethane and the second layer 82 made of the nylon mesh sheet 112 which is easily bent but is not easily stretched, the rotary body 30 is not stretched in the rotational direction, and decrease in the propulsive force due to such stretching is prevented.

Upon rotation of the rotary body 30, the friction force generated between the outer surface 30a and the inner wall surface of the body cavity causes the insertion assisting device 20 and the distal portion 11a to advance along the inner wall surface of the body cavity. At this time, even if the front end of the supporting member 40 comes in contact with the inner wall surface of the body cavity and the inner surface 30b of the rotary body 30 is pressed against the front end surface 51a of the supporting member 40, the first area AR1 and the front end surface 51a are closely-attached to each other, and the convex portion 80 is fitted into and closely-attached to the concave portion 54, such that the first area AR1 and the second area AR2 are on the same plane of the outer surface 30a. Accordingly, the rotary body 30 does not come in point contact with the supporting member 40, and it is possible to prevent the rotary body 30 from stopping rotating due to the pressure concentration caused by the point contact.

When a lesion is found and more concrete inspection is needed, the stop button 26c of the manipulation unit 26 is operated to input instruction for stopping the insertion assisting device 20 to the controller 25. Upon receiving the instruction for stopping the insertion assisting device 20, the controller 25 stops the driving of the motor 24, so as to stop the rotation of the rotary body 30.

Then, after the inspection up to a predetermined position, for example, up to the vicinity of the connecting part between the ascending colon and appendix is completed, the backward button 26b of the manipulation unit 26 is operated to input instruction for retracting the insertion assisting device 20 to the controller 25. Upon receiving the instruction for retracting the insertion assisting device 20, the controller 25 causes the motor 24 to rotate in the direction reverse to the advancing direction, so as to cause the rotary body 30 to rotate in the opposite direction. The insertion assisting device 20 and the distal portion 11a retract, and the insertion section 11 is pulled out from the body cavity of the test subject.

Although the convex portion 80 is provided to the inner surface 30b of the rotary body 30 in the above embodiment, the convex portion 80 may be provided to the outer surface 30a or both of the inner and outer surfaces 30a and 30b. Note that, in the case of providing the convex portion 80 to the outer surface 30a or both of the inner and outer surfaces 30a and 30b, the concave portion 54 may be formed into a shape corresponding to a shape appeared on the inner surface 30b upon being pressed, such that the first area AR1 and the second area AR2 are on almost the same plane of the outer surface 30a.

Although the concave portion 54 is formed in accordance with the shape of the convex portion 80 in the above embodiment, the concave portion 54 does not always have to be formed into the same shape as that of the convex portion 80, as long as it is possible to prevent point contact between the rotary body 30 and the supporting member 40. However, the concave portion 54 preferably has such a shape that the first area AR1 and the second area AR2 are on the same plane of the outer surface 30a when the inner surface 30b of the rotary body 30 comes in contact with the front end surface 51a of the supporting member 40, for the purpose of applying force evenly to the first area AR1 and the second area AR2.

Figure 13:
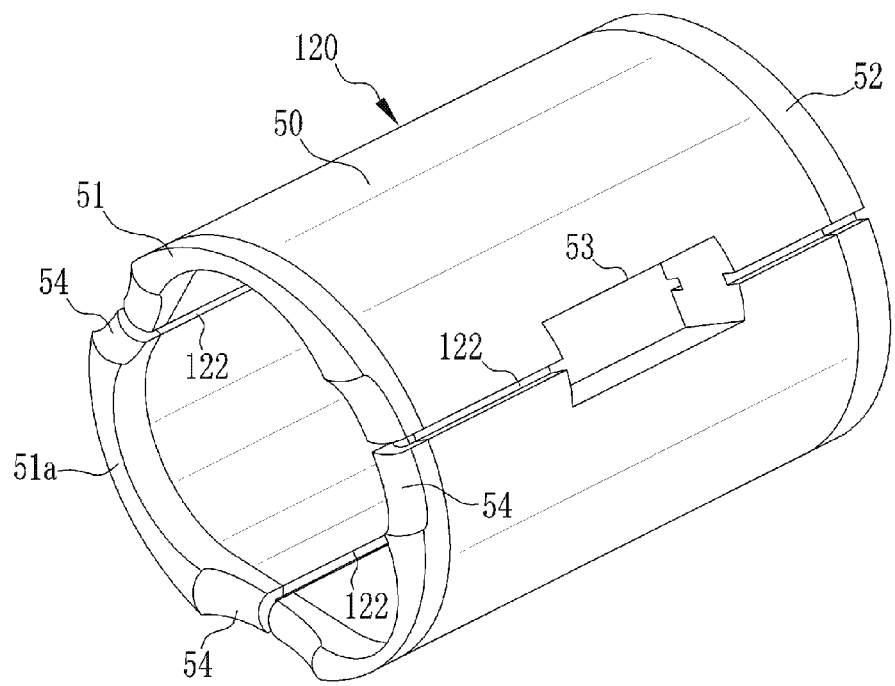
FIG. 13 is a perspective view of a supporting member having streaky grooves formed along the rotational direction.

Although the groove 54a formed in only the front end surface 51a of the supporting member 40 is shown in the above embodiment, a streaky groove 122 may be provided along the rotational direction of the rotary body 30 of a supporting member 120 as shown in FIG. 13. The groove 122 is continuously formed to start from the front end surface, pass through the inner surface, the rear end surface, and the outer surface, and come back again to the front end surface of the supporting member 120. Therefore, it is possible to prevent the rotary body 30 from coming in point contact with the supporting member 120. Additionally, since the rotary body 30 rotates in a state that the protrusion 30e engages with the groove 122, it is possible to prevent the rotary body from rotating in the circumferential direction CD more adequately.

Note that, in the case where the strength of the supporting member 120 is decreased due to the groove 122 formed in both of the inner and outer surfaces, the groove 122 may be formed in any one of the inner and outer surfaces. In such a case, the groove 122 is preferably formed in the inner surface at which positional deviation is likely to occur due to the driving force from each of the driving gears 41.

Figure 14:
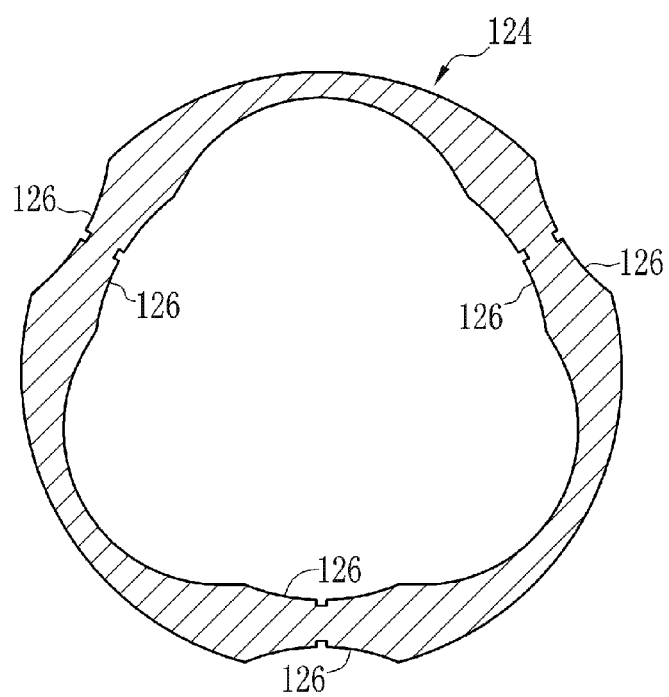
FIG. 14 is a cross-sectional view of a supporting member having concave portions formed on both of inner and outer surfaces thereof.

Although the concave portion 54 is formed only in the front end surface 51a of the supporting member 40 in the above embodiment, a concave portion 126 may be continuously formed in the inner and outer surfaces of a supporting member 124 along the rotational direction of the rotary body 30 as shown in FIG. 14. Thereby, the adhesion degree between the rotary body 30 and the supporting member 124 is increased, and the effect of preventing the rotation of the rotary body 30 in the circumferential direction CD is improved. Additionally, it is possible to remove unnecessary space formed between the concave portion 126 and the convex portion 80. Consequently, it is also possible to make the diameter of the insertion assisting device 20 smaller. Note that, the concave portion 126 may be provided not only in both of the inner and outer surfaces but also in any one of them.

Although the reinforcing portion forming sheet 110 including the main body part 110a and the protection part 110b is overlapped with the rear surface forming sheet 111 having the shape approximately equal to the profile of the rotary body forming sheet 100 in the above embodiment, the shapes of the rotary body forming sheet 100, the reinforcing portion forming sheet 110, and the rear surface forming sheet 111 are not limited thereto.

Figure 15:
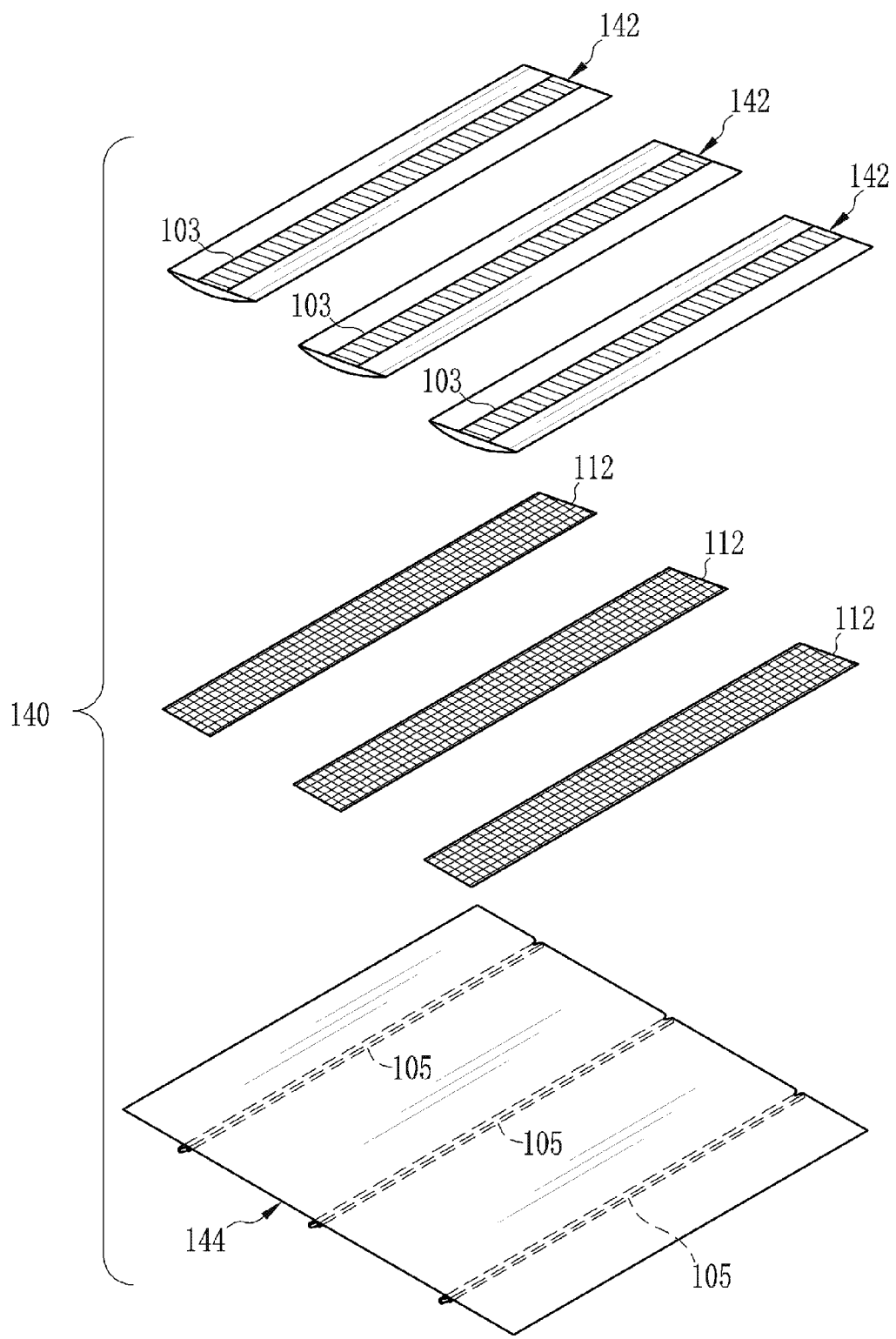
FIG. 15 is an exploded perspective view of a rotary body forming sheet having no stepped portions.

For example, in the case where the stepped portion 104 is not provided to the rotary body forming sheet 100, a rotary body forming sheet 140 shown in FIG. 15 may be adopted. The rotary body forming sheet 140 consists of three reinforcing portion forming sheets 142, a rear surface forming sheet 144, and three nylon mesh sheets 112 which are the same as those in the above embodiment. Each of the reinforcing portion forming sheets 142 consists of only the main body part 110a of the reinforcing portion forming sheet 110 of the above embodiment. The rear surface forming sheet 144 has an approximately rectangular shape corresponding to the shape of the portion extending from the edge portion 100c to the edge portion 104a of the rotary body forming sheet 100 of the above embodiment.

The sheets 112, 142, and 144 are overlapped and adhered or welded to each other to constitute the rotary body forming sheet 140. The rotary body 30 is obtained by adhering or welding the ends of the rotary body forming sheet 140 to each other as in the case of the above embodiment.

Note that, there is fear that the nylon mesh sheet 112 is exposed under the rear end of the reinforcing portion forming sheet 142 and on the reverse side of the front end of the reinforcing portion forming sheet 142 in the rotary body forming sheet 140. However, the exposed portions of the nylon mesh sheet 112 are adhered to each other when the ends of the rotary body forming sheet 140 are overlapped and adhered or welded to each other, and these portions are sandwiched between the reinforcing portion forming sheet 142 and the rear surface forming sheet 144 to be hidden therebetween after the rotary body 30 is formed. Therefore, even if the nylon mesh sheet 112 is exposed in the rotary body forming sheet 140, there arise no substantial problems.

Although the rotary body 30 is in the form of toroid in the above embodiment, the shape of the rotary body 30 is not limited thereto. The rotary body 30 may be a belt which has an end or is endless. In this case, plural belts are used. When the belt which has an end is used, as in the case of a magnetic tape of a cassette tape, for example, a belt is wound around one rotating shaft in a rolled manner, and the belt is caused to move while being wound around the other rotating shaft. Thereby, propulsive force for assisting insertion of the insertion section 11 is obtained.

The driving gear 41 which is a worm wheel is used as a driving member to drive the rotary body 30 in the above embodiment. However, instead of this, the gear barrel 42 may be used as the driving member to drive the rotary body 30 with use of the worm 60. Further, as the driving member, a roller whose peripheral surface is flat or bumpy or the like may be used.

A pressing member may be not only the driven roller 56 but also a solid member in the shape of plate or bar having a smooth surface with less friction. Further, in the case where such a solid member is used as the pressing member, it is preferable that the pressing member is pressed against the rotary body 30 by an elastic body such as a spring.

The number of positions for transmitting the driving force to the rotary body 30 by the driving member may be one, two, or four or more.

Although the cross-section of each of the holding member 43 and the other members has an approximately triangular shape in the above embodiment, it may have a circular shape or other polygonal shapes such as quadrangular shape or hexagonal shape. The cross-sections of the holding member 43 and the other members may be arbitrarily selected in accordance with the position for transmitting the driving force and the number of the position for transmitting the driving force.

The supporting member 40 may have a tubular shape having a polygonal cross-section, instead of the cylindrical shape. Although the main body 50 of the supporting member 40 is made of the metal material in the above embodiment, the main body 50 may be made of a resin material as long as it can retain the strength of the supporting member 40. If the main body 50 is also made of a resin material, it is possible to achieve reduction in cost of the insertion assisting device 20, and the insertion assisting device 20 can be intended for single-use. Further, although the supporting member 40 consists of the main body 50 and the contact protecting portions 51 and 52 respectively attached to the ends of the main body 50 in the above embodiment, the supporting member 40 may be one cylindrical member integrally formed of the resin material or the metal material.

Although the drive control device 21 includes the motor 24 as the power source and the driving force of the motor 24 is transmitted to the insertion assisting device 20 through the torque wire 22 in the above embodiment, the present invention is not limited thereto. The power source such as a motor may be provided inside the insertion assisting device 20. In such a case, the number of the power sources may be one or two or more. Further, the power source is not limited to the motor, and may be anything capable of generating the driving force, such as an actuator.

Furthermore, the pressing members are disposed in the space inside the rotary body 30, and the driving members are disposed outside the rotary body 30 in the above embodiment. However, in the case of disposing the power source inside the insertion assisting device 20, the driving members may be disposed in the space inside the rotary body 30 and the pressing members may be disposed outside the rotary body 30.

Although the present invention is applied to the endoscope for medical diagnosis in each of the above embodiments, the present invention is not limited to the application for the medical diagnosis, and may be applied to an endoscope or a probe for industrial and other purposes.

What is claimed is:

1. An endoscope insertion assisting device comprising:
   a supporting member having an approximately cylindrical shape;
   a rotary body formed into a toroid or a belt, said rotary body being wound over said supporting member and supported in a rotatable manner so as to rotate inside and outside said supporting member in a circulating manner, and said rotary body including a first area continuously formed to have a fixed thickness along the rotational direction and a second area continuously formed to have a convex portion projected more than said first area along the rotational direction, and said second area having an increased thickness so as to make strength thereof higher than that of said first area;
   a concave portion disposed on a front end surface of said supporting member so as to guide said convex portion;
   a driving member disposed so as to come in contact with said second area of said rotary body, said driving member transmitting driving force for rotating said rotary body to said rotary body;
   a pressing member disposed so as to face said driving member across said rotary body, said pressing member pressing said rotary body against said driving member such that the driving force from said driving member is adequately transmitted to said rotary body; and
   an attachment portion for detachably attaching said supporting member to an insertion section of an endoscope in a state that the rotational direction of said rotary body is approximately coincident with an insertion direction of said insertion section, wherein
   said concave portion is formed to have a shape corresponding to said convex portion, such that said first area and said second area form an approximately same plane of an outer surface of said rotary body, when an inner surface of said rotary body comes in contact with the front end surface of said supporting member.

2. The endoscope insertion assisting device as defined in claim 1, wherein said convex portion is provided with a streaky protrusion protruding along the rotational direction, and said concave portion is provided with a groove having a shape corresponding to said protrusion.

3. The endoscope insertion assisting device as defined in claim 2, wherein said groove is continuously formed in an inner surface of said supporting member.

4. The endoscope insertion assisting device as defined in claim 2, wherein said driving member is a worm wheel, and said pressing member is a driven roller attached to said supporting member.

5. The endoscope insertion assisting device as defined in claim 4, wherein said driven roller is provided with a groove having a small diameter for receiving said protrusion of said rotary body.

6. The endoscope insertion assisting device as defined in claim 5, further comprising:
   a gear barrel rotating by driving force from an external driving source;
   a worm formed at an outer periphery of said gear barrel so as to rotate said worm wheel; and
   a cylindrical holding member disposed between said gear barrel and said supporting member so as to hold said driving member in a state that said diving member is exposed through an outer surface of said holding member.

7. The endoscope insertion assisting device as defined in claim 6, wherein said attachment portion has a shaft barrel for supporting said gear barrel in a rotatable manner.

8. The endoscope insertion assisting device as defined in claim 1, wherein a cross-sectional shape of said convex portion is a circular arc in which a height thereof is the largest at the center in a direction approximately orthogonal to the rotational direction and the height thereof is gradually decreased toward both side ends.

9. The endoscope insertion assisting device as defined in claim 1, wherein said rotary body is formed into a toroid, and provided with a plurality of said first areas and a plurality of said second areas alternately arranged in a circumferential direction thereof, and a plurality of said driving members and a plurality of said pressing members are provided so as to correspond to each of said second areas.

10. The endoscope insertion assisting device as defined in claim 1, wherein said first area consists of only a first layer made of a resin material having bendability and flexibility, and said second area includes:

said first layer; and a second layer having a low flexural modulus and a high tensile modulus so as to prevent said first layer from being stretched in the rotational direction.

11. The endoscope insertion assisting device as defined in claim 10, wherein said rotary body is disposed such that said first layer comes in contact with said driving member.

12. The endoscope insertion assisting device as defined in claim 10, wherein said second area further includes a third layer made of said resin material, and said second layer is sandwiched between said first and third layers to form a three-layer structure in said second area.

13. The endoscope insertion assisting device as defined in claim 12, wherein said second layer is formed of a nylon mesh sheet.

14. The endoscope insertion assisting device as defined in claim 1, wherein said supporting member includes:

a main body made of a metal material or a resin material; and a pair of contact protecting portions made of a resin material and attached to a front end and a rear end of said main body, said contact protecting portion attached to the front end of said main body having said concave portion.

* * * * *